United States Patent [19]

Mitta et al.

[11] Patent Number: 5,756,339
[45] Date of Patent: May 26, 1998

[54] HYPERTHERMOSTABLE PROTEASE GENE

[75] Inventors: Masanori Mitta, Tsuzuki-gun; Katsuhiko Yamamoto; Mio Morishita, both of Otsu; Kiyozo Asada, Koka-gun; Susumu Tsunasawa, Kusatsu; Ikunoshin Kato, Uji, all of Japan

[73] Assignee: Takara Shuzo Co., Ltd., Kyoto, Japan

[21] Appl. No.: 750,532

[22] PCT Filed: Jun. 5, 1995

[86] PCT No.: PCT/JP95/01095

§ 371 Date: Dec. 13, 1996

§ 102(e) Date: Dec. 13, 1996

[87] PCT Pub. No.: WO95/34645

PCT Pub. Date: Dec. 21, 1995

[30] Foreign Application Priority Data

Jun. 13, 1994 [JP] Japan ................................. 6-130236
Jul. 26, 1994 [JP] Japan ................................. 6-173912

[51] Int. Cl.⁶ ........................... C07H 21/04; C12N 1/20; C12N 9/50; C12N 9/52
[52] U.S. Cl. ................ 435/220; 435/219; 435/252.3; 435/320.1; 435/325; 536/23.2
[58] Field of Search ..................... 435/219, 220, 435/320.1, 240.1, 252.3, 325; 536/23.2; 935/22

[56] References Cited

U.S. PATENT DOCUMENTS 5,242,817  9/1993  Kelly et al. .............................. 435/220
5,391,489  2/1995  Kelly et al. .............................. 435/220

FOREIGN PATENT DOCUMENTS 6-197770  7/1994  Japan .

OTHER PUBLICATIONS

Ilse I. Blumentals et al, "Charaterization of Sodium Dodecyl Sulfate-Resistant Proteolytic Activity in the Hyperthermophilic Archaebacterium",Applied and Environmental Microbiology, vol. 56, pp. 1992–1998, 1990.

Rik Eggen et al, "Characterization of pyrolysin, a hyperthermoactive serine protease from the archaebacteruim Pyrococcus furiosus".FEMS Microbiology Letter, vol. 71, pp. 17–20, 1990.

Helen Connaris et al, "Heterogeneity of proteinases from the hyperthermophilic archaeobacterium pyrococcus furiosus", Journal of General Microbiology, vol. 137, pp. 1193–1199, 1991.

Michael Klingegerg et al, "Properties of extremely thermostable proteeases from anaerobic hyperthermophilic bacteria", Applied Microbiology and Biotechnology, vol. 34, pp. 715–719, 1991.

Roland J. Siezen et al, "Homology modelling and protein engineering strategy of subtilases, the family of subtilisin--like serine proteinases", Protein Engineering, vol. 4, pp. 719–737 1991.

Robinson et al. (1995) A gene from the hyperthermophile Pyrococcus furiosus whose deduced product is homologous to members of the prolyl oligopeptidase family of proteases, Gene 152: 103–106, Jan. 11, 1995.

Voorhoorst et al. (1996) Isolation and Characterization of the Hyperthermostable Serine Protease, Pyrolysin, and Its Gene from the Hyperthermophilic Archaeon Pyrococcus furiosus, J. Biol. Chem. 271 (34): 20426–20431, Aug. 23, 1996.

Primary Examiner—Robert A. Wax
Assistant Examiner—Einar Stole
Attorney, Agent, or Firm—Browdy and Neimark

[57] ABSTRACT

There is disclosed a hyperthermostable protease gene originating in *Pyrococcus furiosus*, in particular, a hyperthermostable protease gene encoding the amino acid sequence represented by the SEQ ID NO 1 in the Sequence Listing or a part thereof which retains the activity of the hyperthermostable protease. There is also disclosed a process for producing the protease by culturing a transformant transformed with a plasmid into which the above gene has been inserted.

7 Claims, 9 Drawing Sheets

```
             170                 175                 180
   Asp Gly Ser Gly Val Val Val Ala Val Leu Asp Thr Gly Val
   5'-GAT GGT AGT GGT GTT GTT GTT GCA GTA CTT GAC ACG GGA GTT-3'

PRO-1F  5'-GGW WSD RRT GTT RRH GTH GCD GTD MTY GAC ACS GG-3'
```

Fig. 11

```
                   365                    370                    375
       His Gly His Gly Thr His Val Ala Gly Thr Val Ala Gly Tyr
    5'-CAC GGT CAC GGA ACT CAC GTA GCT GGA ACT GTT GCT GGT TAC-3'

PRO-2F  5'-KST CAC GGA ACT CAC GTD GCB GGM ACD GTT GC-3'
PRO-2R     3'-GTG CCT TGA GTG CAH CGV CCK TGH CAA CGM CSA-5'
```

Fig. 12

```
                   590                    595
       Ser Gly Thr Ser Met Ala Thr Pro His Val Ser Gly Val Val
    5'-TCT GGA ACT TCG ATG GCT ACT CCA CAT GTC AGC GGT GTC GTT-3'

PRO-4R  3'-CCD TGV AGB TAC CGD WGA GGB GTR CAV YSG CCH C-5'
```

HYPERTHERMOSTABLE PROTEASE GENE

FIELD OF THE INVENTION

The present invention relates to a gene encoding a hyperthermostable protease which is useful as an enzyme for industrial application and a process for producing the enzyme by genetic engineering.

BACKGROUND OF THE INVENTION

Proteases are enzymes which cleave peptide bonds in proteins and various proteases have been found in animals, plants and microorganisms. They are used not only as reagents for research works and medical supplies, but also in industrial fields such as additives for detergents, food processing and chemical syntheses utilizing their reverse reactions and it can be said that they are very important enzymes from an industrial viewpoint. For proteases to be used in industrial fields, since very high physical and chemical stabilities are required, in particular, enzymes having high thermostability are preferred to use. At present, proteases predominantly used in industrial fields are those produced by bacteria of the genus Bacillus because they have relatively high thermostabilities.

However, enzymes having further superior properties are desired and activities have been attempted to obtain enzymes from microorganisms which can grow at high temperatures, for example, thermophiles of the genus Bacillus.

On the other hand, a group of microorganisms, named as hyperthermophiles, are well adapted themselves to high temperature environment and therefore they are expected to be supply sources for various thermostable enzymes. It has been known that one of these hyperthermophiles, *Pyrococcus furiosus*, produces proteases [Appl. Environ. Microbiol., 56, 1992–1998 (1990); FEMS Microbiol. Letters, 71, 17–20 (1990); J. Gen. Microbiol., 137, 1193–1199 (1991)].

In addition, as for hyperthermophiles of the genera Thermococcus, Staphylothermus and Thermobacteroides, the production of proteases have also been known [Applied Microbiology and Biotechnology, 34, 715–719 (1991)].

OBJECTS OF THE INVENTION

Since proteases produced by these hyperthermophiles have high thermostabilities, they are expected to be applicable to new applications to which any known enzyme has not been utilized. However, the above publications merely teach that thermostable protease activities are present in cell-free extracts or crude enzyme solutions obtained from culture supernatants and there is no disclosure about properties of isolated and purified enzymes and the like. Moreover, since a cultivation of microorganisms at high temperature is required to obtain enzymes from these hyperthermophiles, there is a problem in industrial production of the enzymes.

In order to solve the above problems, an object of the present invention is to isolate a gene encoding a protease of a hyperthermophile. Another object of the present invention is to provide a process for producing the protease by genetic engineering using the gene.

BRIEF DESCRIPTION OF THE DRAWINGS

FIG. 11 illustrates designs of oligonucleotides PRO-2F and PRO-2R.
FIG. 12 illustrates a design of an oligonucleotide PRO-4R.

DISCLOSURE OF THE INVENTION

Figure 1:
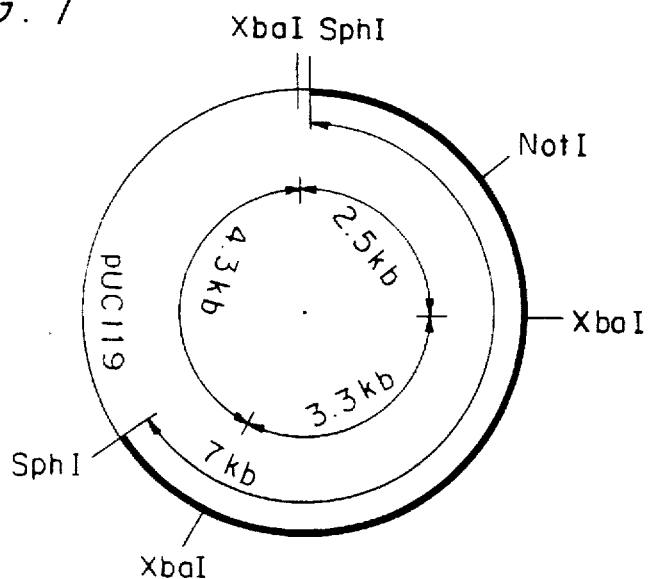
FIG. 1 illustrates a restriction map of the plasmid pTPR1.

In order to obtain a hyperthermostable protease gene, the present inventors attempted to purify a protease from microbial cells and a culture supernatant of *Pyrococcus furiosus* DSM 3638 so as to determine a partial amino acid sequence of the enzyme, independently. However, purification of the protease was very difficult in either case of using the microbial cells or the culture supernatant and the present inventors failed to obtain an enzyme sample having sufficient purity for determination of its partial amino acid sequence.

As a method for cloning a gene for an objective enzyme without any information about a primary structure of the enzyme, there is an expression cloning method and, for example, a pullulanase gene originating in *Pyrococcus woesei* has been obtained according to this method (WO 92/02614). However, in an expression cloning method, a plasmid vector is generally used and, in such case, it is necessary to use restriction enzymes which can cleave an objective gene into relatively small DNA fragments so that the fragments can be inserted into the plasmid vector without cleavage of any internal portion of the objective gene. Then, the method is not always applicable to cloning of all kinds of enzyme genes. Furthermore, it is necessary to test for an enzyme activity of a large number of clones and this operation is complicated.

The present inventors have attempted to isolate a protease gene by using a cosmid vector which can maintain a larger DNA fragment (35–50 kb) instead of a plasmid vector to prepare a cosmid library of *Pyrococcus furiosus* genome and investigating cosmid clones in the library to find out a clone expressing a protease activity. By using a cosmid vector, the number of transformants to be screened can be reduced in addition to lowering of possibilities of cleavage of an internal portion of the enzyme gene. On the other hand, since the copy number of a cosmid vector in a host is not higher than that of a plasmid vector, it may be that an amount of the enzyme expressed is too small to detect its enzyme activity.

In view of high thermostability of the objective enzyme, firstly, the present inventors have cultured respective transformants in a cosmid library, separately, and have combined this step with a step for preparing lysates containing ing only thermostable proteins from the microbial cells thus obtained. This group of lysates have been named as a cosmid protein library. By using the cosmid protein library in detection of the enzyme activity, detection sensitivity can be increased higher than that of a method using transformant colonies.

In addition, the present inventors have made possible to detect a trace amount of the enzyme activity by performing SDS-polyacrylamide gel-electrophoresis with a gel containing gelatin. According to this method, a trace amount of a protease activity contained in a sample can be detected with high sensitivity as a band concentrated in the gel.

In this manner, the present inventors have screened a cosmid protein library originating in *Pyrococcus furiosus* and have obtained several cosmid clones which express the protease activity.

Furthermore, the present inventors have succeeded in isolation of hyperthermostable protease genes from inserted DNA fragments contained in the clones by utilizing various gene engineering techniques and also have found that products expressed from the genes are resistant to surfactants.

By comparing an amino acid sequence of the hyperthermostable protease deduced from the nucleotide sequence of the gene with amino acid sequences of known proteases originating in microorganisms, homology of the amino acid sequence of the front half portion of the protease encoded by the gene with those of a group of alkaline proteases, whose representative example is subtilisin, has been shown and, in particular, very high homology has been found at each region around the four amino acid residues which are known to be of importance for a catalytic activity of the enzymes. Thus, since the protease produced by *Pyrococcus furiosus*, which is active at such high temperatures that proteases originating in mesophiles are readily inactivated, has been shown to retain a structure similar to those of enzymes from mesophiles, it has been suggested that similar proteases would also be produced by hyperthermophiles other than *Pyrococcus furiosus*.

Then, the present inventors have noted possibilities that, in the nucleotide sequence of the hyperthermostable protease gene obtained, the nucleotide sequences encoding regions showing high homology with subtilisin and the like can be used as probes for investigating hyperthermostable protease genes and have attempted to detect protease genes originating in hyperthermophiles by PCR using synthetic DNA designed based on the above nucleotide sequences as primers so as to clone DNA fragments containing the protease genes. As a result, the present inventors have found a protease gene in a hyperthermophile, *Thermococcus celer* DSM2476, and have obtained a DNA fragment containing the gene. Furthermore, the present inventors have confirmed that an amino acid sequence encoded by the DNA fragment contains amino acids sequences having high homology with the amino acid sequences of the hyperthermostable protease represented by SEQ NO 1 of the Sequence Listing. Thus, the present inventors have completed the present invention.

That is, the present invention provides an isolated hyperthermostable protease genes originating in *Pyrococcus furiosus*, in particular, a hyperthermostable protease gene which comprises the amino acid sequence represented by SEQ ID NO 1 in the Sequence Listing or a part thereof encoding the active portion of the hyperthermostable protease, especially, the hyperthermostable protease gene having the DNA sequence represented by SEQ ID NO 2 in the Sequence Listing.

In addition, the present invention provides hyperthermostable protease genes hybridizable with the above hyperthermostable protease genes. For example, there is provided a hyperthermostable protease gene containing the nucleotide sequence represented by SEQ ID NO 7 in the Sequence Listing.

Moreover, the present invention provides a process for producing the hyperthermostable protease which comprising culturing a transformant transformed with a recombinant plasmid into which the hyperthermostable protease gene of the present invention has been inserted, and collecting the hyperthermostable protease from the culture.

The hyperthermostable protease genes of the present invention can be obtained by screening of gene libraries of hyperthermophiles. As the hyperthermophiles, bacteria belonging to the genus Pyrococcus can be used and the desired genes can be obtained by screening a cosmid library of *Pyrococcus furiosus* genome.

For example, *Pyrococcus furiosus* DSM3638 can be used as *Pyrococcus furiosus* and this strain is available from Deutsch Sammlung von Microorganismen und Zellkulturen GmbH.

One example of cosmid libraries of *Pyrococcus furiosus* can be obtained by partially digesting the genomic DNA of *Pyrococcus furiosus* DSM3638 with a restriction enzyme, Sau3AI (manufactured by Takara Shuzo, Co., Ltd.), to obtain DNA fragments, ligating the DNA fragments with a triple helix cosmid vector (manufactured by Stratagene) and packaging into lambda phage particles by in vitro packaging method. Then, the library is transduced into a suitable *E. coli*, for example, *E. coli* DH5αMCR (manufactured by BRL) to obtain transformants, followed by culturing them, collecting the microbial cells, subjecting them to heat treatment (100° C. for 10 minutes), sonicating and subjecting heat treatment (100° C. for 10 minutes) again. The lysates thus obtained can be subjected to screening for the protease activity by performing SDS-polyamide gel-electrophoresis with a gel containing gelatin.

In this manner, a cosmid clone containing a hyperthermostable protease gene capable of expressing a protease which is resistant to the above heat treatment can be obtained.

Furthermore, a cosmid DNA prepared from the above-obtained cosmid clone can be digested with suitable restriction enzymes to form fragments to prepare recombinant plasmids into which the respective fragments thus obtained are inserted. A recombinant plasmid containing the desired hyperthermostable protease gene can be obtained by transforming a suitable microorganism with the above-obtained plasmids and testing for the protease activity expressed by the resultant transformants.

That is, a cosmid DNA prepared from one of the above-obtained cosmid clones can be digested with SphI (manufactured by Takara Shuzo, Co., Ltd.), followed by inserting the resultant DNA fragment into SphI site of a plasmid vector, pUC119 (manufactured by Takara Shuzo, Co., Ltd.) to obtain a recombinant plasmid. Then, the recombinant plasmid is introduced into *E. coli* JM109 (manufactured by Takara Shuzo, Co., Ltd.) and the protease activity of the resultant transformant is tested by the same method as that used for screening of the cosmid protein library. The transformant having the activity is used for preparation of a plasmid.

As is seen from Examples hereinafter, one of the recombinant plasmids has been named as pTPR1 and *E. coli* JM109 transformed with the plasmid has been named as *Escherichia coli* JM109/pTPR1. FIG. 1 illustrates a restriction map of the plasmid pTPR1. In FIG. 1, the thick solid line represents the DNA fragment inserted into the plasmid vector pUC119. The recombinant plasmid contains SphI fragment of about 7.0 kb.

Figure 2:
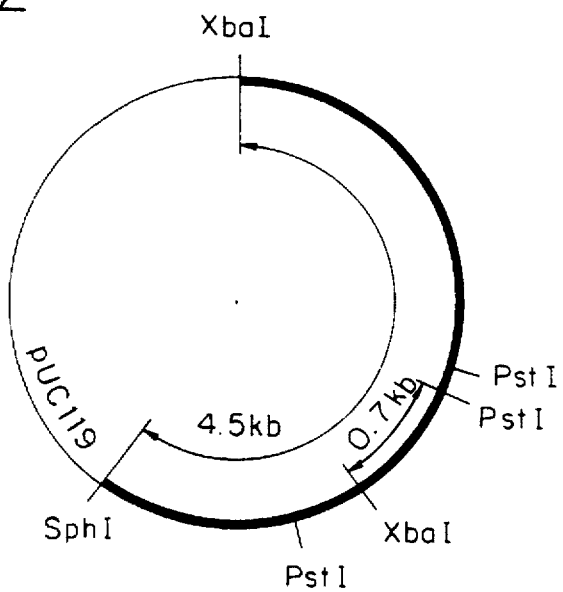
FIG. 2 illustrates a restriction map of the plasmid pTPR9.

In addition, a DNA fragment of about 2.5 kb which does not contain the hyperthermostable protease gene can be removed from the recombinant plasmid. That is, among three fragments of about 2.5 kb, about 3.3 kb and about 4.3 kb obtained by digesting the above plasmid pTPR1 with XbaI (manufactured by Takara Shuzo, Co., Ltd.), only the DNA fragment of about 2.5 kb is removed and the remaining fragments are ligated and introduced into *E. coli* JM109. The protease activity of the resultant transformant is tested by the same method as that used for screening of the cosmid protein library. The resultant transformant having the protease activity is used for preparation of a plasmid. The plasmid has been named as pTPR9 and *E. coli* JM109 transformed with the plasmid has been named as *Escherichia coli* JM109/pTPR9. FIG. 2 illustrates a restriction map of the plasmid pTPR9. In FIG. 2, the thick solid line represents the DNA fragment inserted into the plasmid vector pUC119.

The protease activities expressed by both plasmids pTPR1 and pTPR9 show high thermostability. However, since the activities are observed at positions different from that for the protease activity expressed by above cosmid clone on a SDS-polyacrylamide gel containing gelatin, these plasmids are estimated to be defect in a part of the protease gene on the cosmid DNA. A DNA fragment containing the whole length of the protease gene can be obtained from the cosmid DNA by, for example, using a part of the inserted DNA fragment of the above plasmid pTPR9 as a probe. That is, the cosmid DNA used for preparation of the plasmid pTPR1 is digested with NotI (manufactured by Takara Shuzo, Co., Ltd.) and several restriction enzymes which do not cleave any internal portion of the DNA fragment inserted into the plasmid pTPR1. After agarose gel-electrophoresis, the DNA fragments in the gel are blotted on a nylon membrane. Regarding the membrane thus obtained, hybridization is carried out by using a PstI-XbaI fragment of about 0.7 kb obtained from the DNA fragment inserted into the plasmid pTPR9 as a probe to detect a DNA fragment containing the same sequence as that of the PstI-XbaI fragment.

In the cosmid DNA digested with two enzymes, NotI and PvuII (manufactured by Takara Shuzo Co., Ltd.), a DNA fragment of about 7.5 kb is hybridized with the PstI-XbaI fragment. This fragment of about 7.5 kb can be isolated to insert into a plasmid vector, pUC19 (manufactured by Takara Shuzo, Co., Ltd.) into which NotI linker (manufactured by Takara Shuzo Co., Ltd.) has been introduced at a HincII site, at a site between NotI and SmaI. The plasmid has been named as pTPR12 and *E. coli* JM109 transformed by the plasmid has been named and indicated as *Escherichia coli* JM109/pTPR12. This strain has been deposited with National Institute of Bioscience and Human-Technology (NIBH), Agency of Industrial Science & Technology, Ministry of International Trade & Industry under the accession number of FERM BP-5103 under Budapest Treaty since May 24, 1994 (the date of the original deposit).

Figure 3:
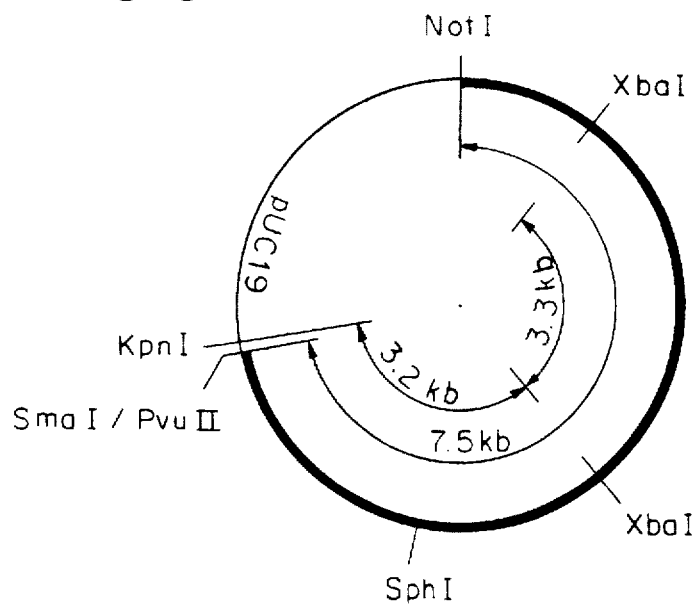
FIG. 3 illustrates a restriction map of the plasmid pTPR12.

A lysate of *Escherichia coli* JM109/pTPR12 shows the protease activity similar to that of the cosmid clone on a SDS-polyacrylamide gel containing gelatin. FIG. 3 illustrates a restriction map of the plasmid pTPR12. In FIG. 3, the thick solid line is the DNA fragment inserted into the plasmid vector pUC19.

Figure 4:
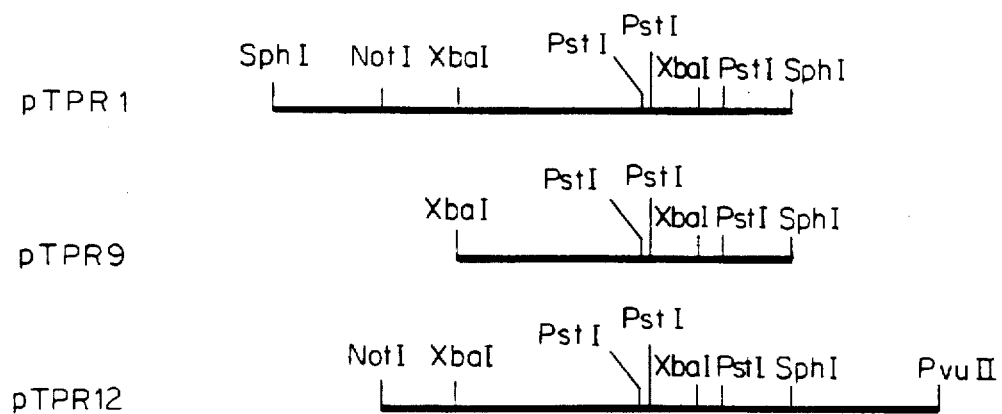
FIG. 4 illustrates comparison of restriction maps of DNA's derived from *Pyrococcus furiosus* contained in the plasmids.
Figure 5:
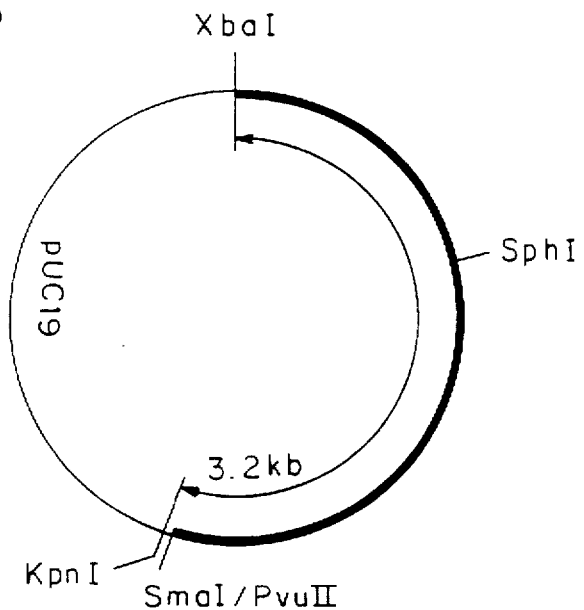
FIG. 5 illustrates a restriction map of the plasmid pTPR15.

FIG. 4 illustrates restriction maps of the DNA fragments originating in *Pyrococcus furiosus* which are inserted into the plasmids pTPR1, pTPR9 and pTPR12, respectively. According to FIG. 4, a fragment of about 1 kb which does not contain a hyperthermostable protease gene can be removed from the DNA fragment inserted into the plasmid pTPR12. That is, the plasmid pTPR12 is digested with XbaI and KpnI (manufactured by Takara Shuzo, Co., Ltd.) and thus-obtained XbaI-XbaI fragment of about 3.3 kb and XbaI-KpnI fragment of about 3.2 kb are isolated, respectively. Then, firstly, the XbaI-KpnI fragment of about 3.2 kb is inserted into the plasmid vector pUC19 at a site between XbaI and KpnI to prepare a recombinant plasmid. This plasmid has been named as pTPR14 and FIG. 5 illustrates its restriction map. In FIG. 5, the thick solid line represents the DNA fragment inserted into the plasmid vector pUC19.

Figure 6:
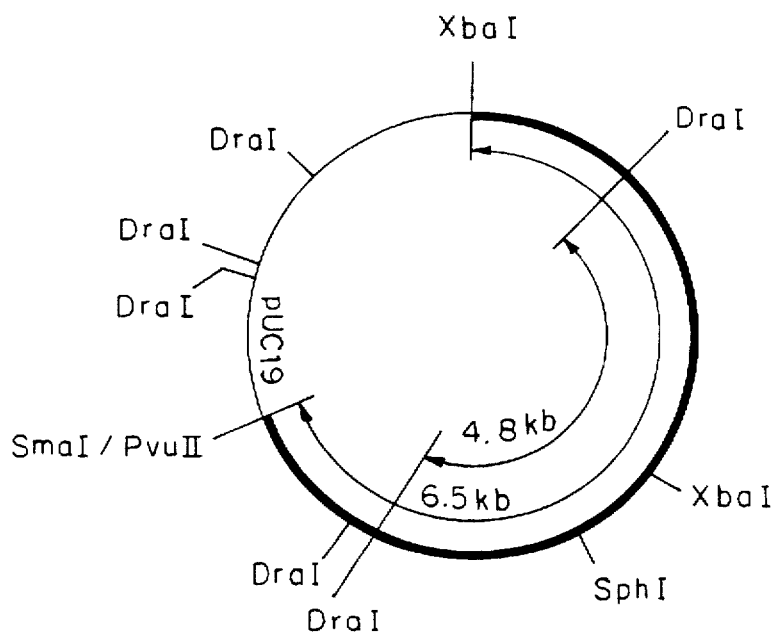
FIG. 6 illustrates a restriction map of the plasmid pTPR15.

Then, the above XbaI-XbaI fragment of about 3.3 kb is inserted into the plasmid pTPR14 at XbaI site and introduced into *E. coli* JM109. The protease activity of the transformant is tested by using the method used for screening the cosmid protein library. A plasmid is prepared by the transformant having the activity. The plasmid has been named as pTPR15 and *E. coli* JM109 transformed with the plasmid has been named as *Escherichia coli* JM109/pTPR15. FIG. 6 illustrates a restriction map of pTPR15. In FIG. 6, the thick solid line represents the DNA fragment inserted into the plasmid vector pUC19.

Further, in the nucleotide sequences of the DNA fragment originating in *Pyrococcus furiosus* and inserted into the plasmid pTPR15, the nucleotide sequence of the DNA fragment of about 4.8 kb between two DraI sites are shown as SEQ ID NO 8 in the Sequence Listing. That is, SEQ ID NO 8 of the Sequence Listing is an example of the nucleotide sequence of the hyperthermostable protease gene of the present invention. And, an amino acid sequence of a product of the gene deduced from the nucleotide sequence of SEQ ID NO 8 is shown as SEQ ID NO 9 in the Sequence Listing. That is, SEQ ID NO 9 in the Sequence Listing is an example of the amino acid sequence of an enzyme protein produced by using the hyperthermostable protease gene obtained according to the present invention.

Because it has been found that the hyperthermostable protease gene of the present invention is contained in DraI fragment of about 4.8 kb in the DNA fragment inserted into the above plasmid pTPR15, a recombinant plasmid containing only this DraI fragment can be prepared.

That is, the above plasmid pTPR15 is digested with DraI (manufactured by Takara Shuzo Co., Ltd.) to isolate the resultant DNA fragment of about 4.8 kb. Then, it can be inserted into the plasmid vector pUC19 at SmaI site to prepare a recombinant plasmid. The recombinant plasmid has been named as pTPR13 and *E. coli* JM109 transformed with the plasmid has been named as *Escherichia coli* JM109/pTPR13.

Figure 7:
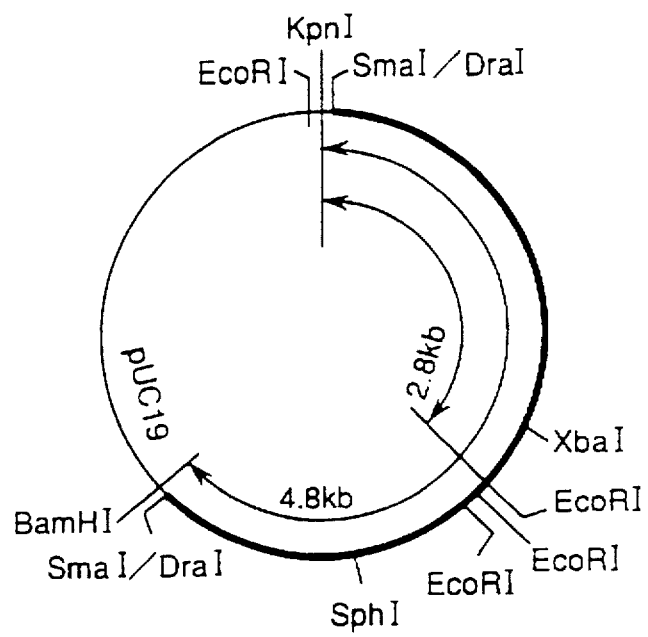
FIG. 7 illustrates a restriction map of the plasmid pTPR13.

A lysate of *Escherichia coli* JM109/pTPR13 shows the same protease activity as that of the cosmid clone on a SDS-polyacrylamide gel containing gelatin. FIG. 7 illustrates a restriction map of the plasmid pTPR13. In FIG. 7, the thick solid line represents the DNA fragment inserted into the plasmid vector pUC19.

In addition, the hyperthermostable protease gene of the present invention can be expressed in *Bacillus subtilis*. As the *Bacillus subtilis*, *Bacillus subtilis* DB104 can be used and this strain is a known strain described in Gene, Vol. 83, pp. 215–233 (1989). As a cloning vector, a plasmid pUB18-P43 can be used and this plasmid has been given by Dr. Sui-Lam Wong of Calgary University. This plasmid contains a kanamycin resistant gene as a selection marker.

Figure 8:
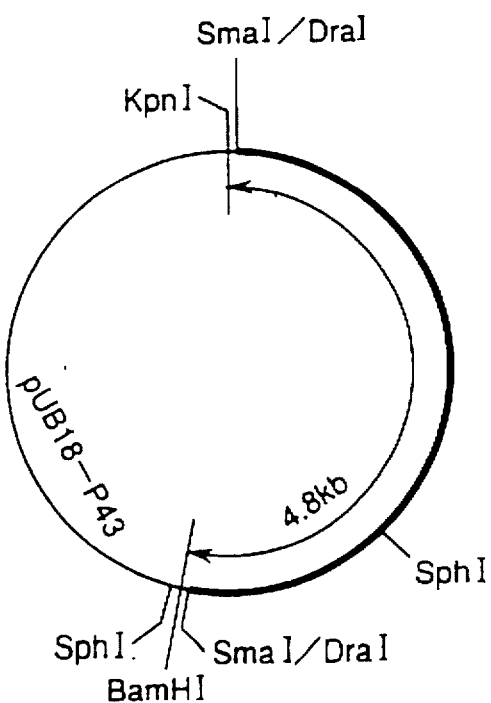
FIG. 8 illustrates a restriction map of the plasmid pUBR13.

The above-described plasmid pTPR13 can be digested with KpnI (manufactured by Takara Shuzo Co., Ltd.) and BamHI (manufactured by Takara Shuzo Co., Ltd.) to obtain a DNA fragment of about 4.8 kb, followed by isolating and ligating the fragment between KpnI site and BamHI site of the plasmid pUB18-P43 to prepare a recombinant plasmid. The plasmid has been named as pUBP13 and *Bacillus subtilis* DB104 transformed with the plasmid has been named as *Bacillus subtilis* DB104/pUBP13. A lysate of *Bacillus subtilis* DB104/pUBP13 shows the same protease activity as that of the cosmid clone on a SDS-polyacrylamide gel containing gelatin. FIG. 8 illustrates a restriction map of the plasmid pUBP13. In Fig. 8, the thick solid line represents the DNA fragment inserted into the plasmid vector pUB18-P43.

By comparing the amino acid sequence shown by SEQ ID NO 9 of the Sequence Listing with amino acid sequences of proteases originating in known microorganisms, it is shown that there is homology between the front half portion of the sequence of the hyperthermostable protease of the present invention and those of a group of alkaline serine proteases whose representative example is subtilisin [Protein Engineering, Vol. 4, pp. 719–737 (1991)], in particular, there is high homology between each region around the four amino acid residues which are known to be of importance for protease activity. On the other hand, such homology cannot be observed between the back half portions of the amino acid sequences and it is considered that this portion may not be essential to a protease activity. Therefore, a mutant protease wherein an appropriate peptide chain is removed from its back half portion is expected to show the enzymatic activity. Examples of such mutant protease include a protease having an amino acid sequence corresponding to SEQ ID. NO 9 of the Sequence Listing from which the 904th amino acid, Ser, and the subsequent sequence has been removed. This can be prepared by the following process.

Figures 9, 10:
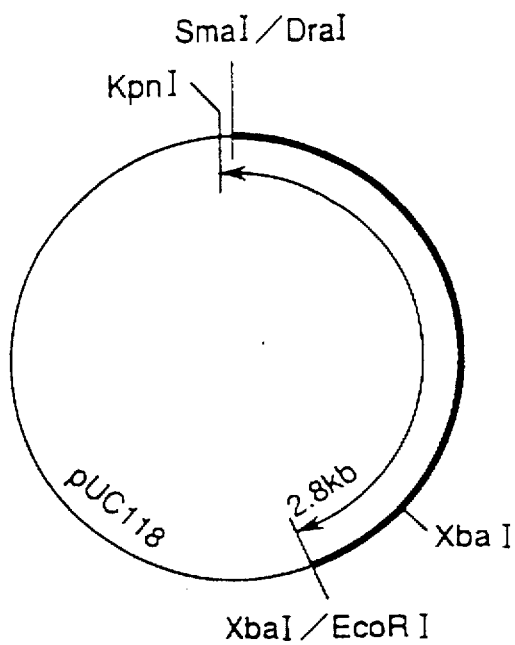
FIG. 9 illustrates a restriction map of the plasmid pUBR36.
FIG. 10 illustrates a design of an oligonucleotide PRO-1F.

Firstly, a KpnI-EcoRI fragment of about 2.8 kb wherein the EcoRI site is blunted is prepared from the above plasmid pTPR13 and the fragment is ligated between the KpnI site and the blunted XbaI site of the plasmid vector pUC119. A protease gene contained in the recombinant plasmid thus obtained encodes an amino acid sequence corresponding to the SEQ ID NO 9 of the Sequence Listing except that the nucleotide sequence TCA encoding the 904th amino acid, Ser, has been replaced with the termination codon TAG and the subsequent nucleotide sequence has been deleted. The plasmid has been named as pTPR36 and *E. coli* JM109 transformed with the plasmid has been named *Escherichia coli* JM109/pTPR36. A lysate of *Escherichia coli* JM109/pTPR36 shows an protease activity on a SDS-polyacrylamide gel containing gelatin. FIG. 9 illustrates a restriction map of the plasmid pTPR36. In FIG. 9, the thick solid line represents the DNA fragment inserted into the plasmid vector pUC119. SEQ ID NO 2 in the Sequence Listing is a nucleotide sequence of the open reading frame contained in the DNA fragment inserted in the plasmid pTPR36. That is, SEQ ID NO 2 of the Sequence Listing is an example of nucleotide sequences of the hyperthermostable protease genes obtained in the present invention. In addition, SEQ ID NO 1 of the Sequence Listing is an amino acid sequence of the gene product deduced from the nucleotide sequence of SEQ ID NO 2. That is, SEQ ID NO 1 of the Sequence Listing is an example of amino acid sequences of enzyme proteins produced by using hyperthermostable protease genes obtained by the present invention.

As described above, it has been found that the regions commonly present in alkaline serine proteases originating in mesophiles are conserved in the amino acid sequence of the hyperthermostable protease produced by the hyperthermophile *Pyrococcus furiosus*. Therefore, the presence of the regions is expected in the same kind of proteases produced by hyperthermophiles other than *Pyrococcus furiosus*. That is, it is possible to obtain genes for hyperthermostable proteases similar to the above-described hyperthermostable protease by preparing suitable synthetic DNA fragments based on parts of the nucleotide sequence of SEQ ID NO 2 of the Sequence Listing which encode amino acid sequences having high homology with those of subtilisin and the like, and using them as probes or primers.

FIGS. 10, 11 and 12 illustrate the relation among the amino acid sequences of regions in the amino acid sequence of the hyperthermostable protease of the present invention which have high homology with those of subtilisin and the like, the nucleotide sequences of the hyperthermostable protease gene of the present invention which encode the regions, and the nucleotide sequences of oligonucleotides PRO-1F, PRO-2F, PRO-2R and PRO-4R synthesized based on the above sequences, respectively. In addition, SEQ ID NO 3, 4, 5 and 6 of the Sequence Listing illustrate the nucleotide sequences of the oligonucleotides PRO-1F, PRO-2F, PRO-2R and PRO-4R. That is, SEQ ID NO 3, 4, 5 and 6 of the Sequence Listing are examples of oligonucleotides which can be used for detection of the hyperthermostable protease genes of the present invention by hybridization.

A combination of above oligonucleotides can be used as primers to carry out PCR using genomic DNA of various hyperthermophiles as templates to detect protease genes present in hyperthermophiles. As the hyperthermophiles, bacteria belonging to the genera Pyrococcus, Thermococcus, Staphylothermus, Thermobacteroides and the like can be used. As bacteria belonging to the genus Thermococcus, Thermococcus celer DSM2476 can be used and the strain is available from Deutsch Sammlung von Microorganismen und Zellkulturen GmbH. When PCR is carried out by using genomic DNA of *Thermococcus celer* DSM2476 as a template and a combination of the above oligonucleotides PRO-1F and PRO-2R or a combination of PRO-2F and PRO-4R as primers, specific amplification of DNA fragments is observed and the presence of a protease gene can be indicated. In addition, an amino acid sequence encoded by the fragment can be estimated by ligating the fragment to suitable plasmid vector to prepare a recombinant plasmid and determining the nucleotide sequence of the inserted DNA fragment by dideoxy method.

A DNA fragment of about 150 bp amplified by using the oligonucleotides PRO-1F and PRO-2R and a DNA fragment of about 550 bp amplified by using the oligonucleotides PRO-2F and PRO-4R are ligated to HincII site of the plasmid vector pUC18 to obtain recombinant plasmids, respectively. The recombinant plasmids have been named as p1F-2R(2) and p2F-4R, respectively. SEQ ID NO 10 of the Sequence Listing illustrates the nucleotide sequence of the DNA fragment inserted into the plasmid p1F-2R(2) and an amino acid sequence deduced therefrom. SEQ ID NO 11 of the Sequence Listing illustrates the nucleotide sequence of the DNA fragment inserted into the plasmid p2F-4R and an amino acid sequence deduced therefrom. In the nucleotide sequence shown by SEQ ID NO 10 of the Sequence Listing, the sequence from the 1st to the 21st nucleotides and the sequence from the 113th to the 145th nucleotides and, in the nucleotide sequence shown by SEQ ID NO 11 of the Sequence Listing, the sequence from the 1st to the 32nd nucleotides and the sequence from the 532nd to the 564th nucleotides are the nucleotide sequences derived from the oligonucleotides used as the primers (corresponding to the oligonucleotides PRO-1F, PRO-2R, PRO-2F and PRO-4R, respectively). In the amino acid sequences shown by SEQ ID NO 10 and 11, there are sequences having homology with amino acid sequences of the hyperthermostable protease originating in *Pyrococuss furiosus* of the present invention as well as alkaline serine protease originating in various microorganisms and it has been shown that the above DNA fragments amplified by PCR are those amplified utilizing the protease gene as the template.

Figure 13:
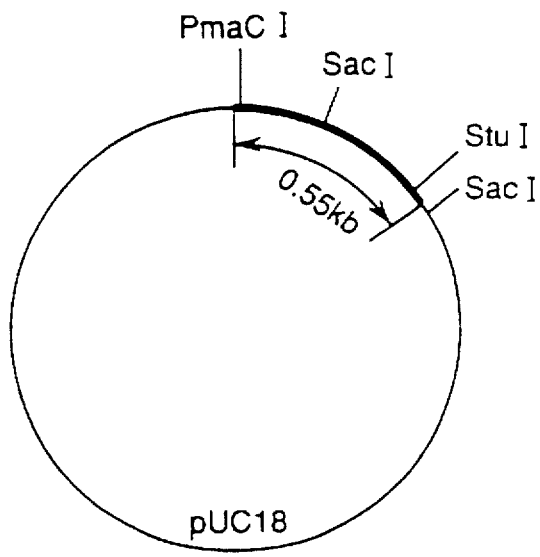
FIG. 13 illustrates a restriction map of the plasmid p2F-4R.

FIG. 13 illustrates a restriction map of the plasmid p2F-4R. In FIG. 13, the thick solid line represents the DNA fragment inserted into the plasmid vector pUC18.

On the other hand, when genomic DNA of *Thermobacteroides proteoliticus* DSM5265 and *Staphylothermus marinus* DSM3639 are used as templates, amplification as observed in case of *Thermococcus celer* has not been recognized.

It has been known that efficiency of gene amplification by PCR is influenced by annealing efficiency of a 3'-terminal portion of a primer and a template DNA. Even when amplification of DNA fragment is not observed in the above PCR, protease genes can be detected by synthesizing oligonucleotides having different sequences but encoding the same amino acid sequence and using them as primers. In addition, protease genes can also be detected by using these oligonucleotides as probes and carrying out Southern hybridization with genomic DNA of various hyperthermophiles.

Then, the above-described oligonucleotides or amplified DNA fragments obtained by the above PCR can be used as probes for screening genomic DNA libraries of hyperthermophiles to obtain hyperthermostable protease genes, for example, the hyperthermostable protease gene produced by *Thermococcus celer*.

As an example of genomic DNA libraries of *Thermococcus celer*, there is a library prepared by partially digesting a genomic DNA of *Thermococcus celer* DSM2476 with a restriction enzyme Sau3AI to obtain a DNA fragment, ligating the fragment with lambda GEM-11 vector (manufactured by Promega) and packaging it into lambda phage particles according to in vitro packaging method. Then, the library is transduced into a suitable *E. coli*, for example, *E. coli* LE392 (manufactured by Promega) to form plaques on a plate and then plaque hybridization is carried out by using amplified DNA fragments obtained in the above-described PCR. In this manner, phage clones containing hyperthermostable protease genes can be obtained.

Further, the phage DNA prepared from the clone thus obtained is digested with suitable restriction enzymes and, after subjecting to agarose gel-electrophoresis, DNA fragments in the gel are blotted on a nylon membrane. Regarding the membrane thus obtained, hybridization is carried out using amplified DNA fragments obtained according to the above PCR as probes to detect a DNA fragments containing the protease gene.

When the above phage DNA is digested with KpnI, a DNA fragment of about 9 kb is hybridized with the probe and this fragment of about 9 kb can be isolated and inserted into KpnI site of the plasmid vector pUC119 to obtain a recombinant plasmid. This plasmid has been named as pTC1 and *E. coli* JM109 transformed with this plasmid has been named as *Escherichia coli* JM109/pTC1.

Figure 14:
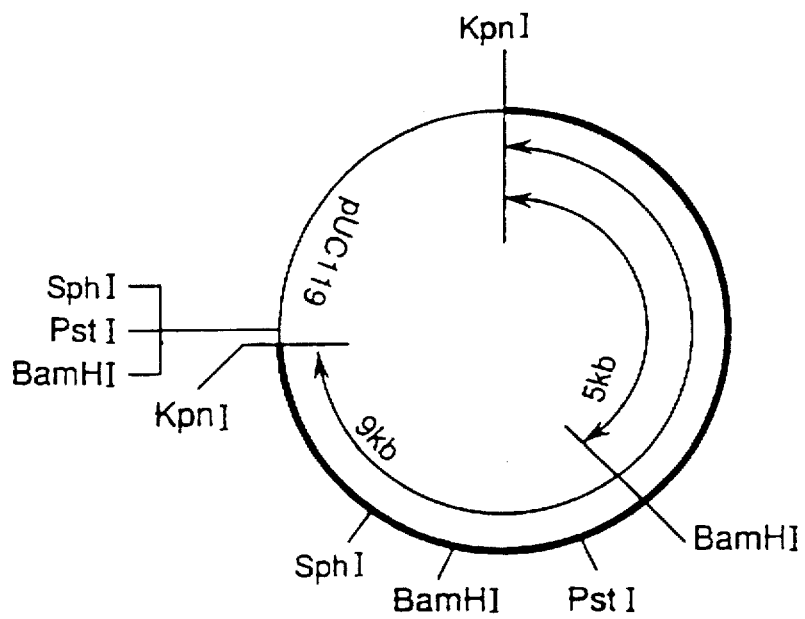
FIG. 14 illustrates a restriction map of the plasmid pTC1.

FIG. 14 illustrates a restriction map of the plasmid pTC1. In FIG. 14, the thick solid line represents the DNA fragment inserted into the plasmid vector pUC119.

Figure 15:
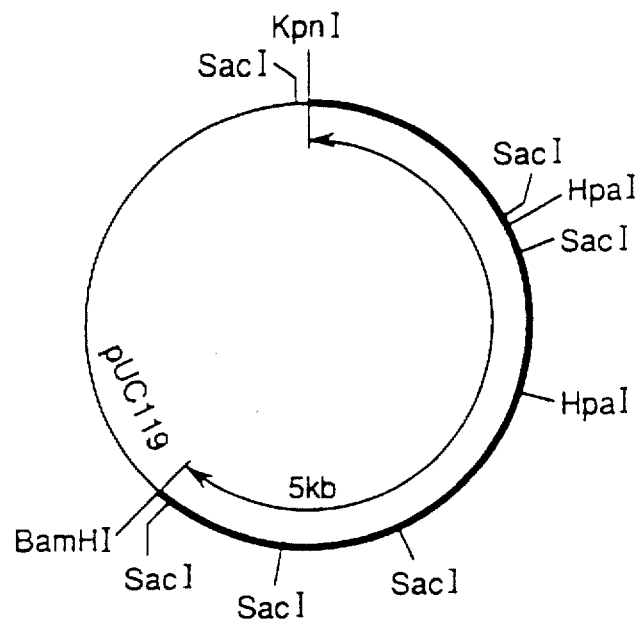
FIG. 15 illustrates a restriction map of the plasmid pTC3.

Furthermore, a DNA fragment of about 4 kb which does not contain the hyperthermostable protease gene can be removed from the plasmid pTC1. That is, plasmid pTC1 is digested with KpnI and several restriction enzymes which cleave the region within the fragment inserted into the plasmid pTC1 and, after subjecting to agarose gel-electrophoresis, detection of a DNA fragment containing the protease gene is carried out according to the same manner as that for the above phage DNA. When the plasmid pTC1 is digested with KpnI and BamHI, a DNA fragment of about 5 kb is hybridized with the probe and this fragment of about 5 kb can be isolated and introduced into KpnI-BamH site of the plasmid vector pUC119 to obtain a recombinant plasmid. This plasmid has been named as pTC1 and *E. coli* JM109 transformed with this plasmid has been named as *Escherichia coli* JM109/pTC3. FIG. 15 illustrates a restriction map of the plasmid pTC3. In FIG. 15, the thick solid line represents the DNA fragment inserted into the plasmid vector pUC119.

The nucleotide sequence of the hyperthermostable protease gene contained in the DNA fragment inserted into the plasmid pTC3 can be determined by using specific primers, i.e., by using suitable oligonucleotides synthesized based on the nucleotide sequences as shown by SEQ ID NO 10 and 11 of the Sequence Listing as primers. SEQ ID NO 12, 13, 14, 15, 16 and 17 represent the nucleotide sequences of the oligonucleotides TCE-2, TCE-4, SEF-3, SER-1, SER-3 and TCE-6R which have been used as the primers for determination of the nucleotide sequence of the hyperthermostable protease gene. In addition, SEQ ID NO 7 of the Sequence Listing represents a part of the nucleotide sequence of the hyperthermostable protease gene thus obtained. That is, SEQ ID NO 7 is a part of the nucleotide sequence of the hyperthermostable protease gene of the present invention. Moreover, SEQ ID NO 18 represents an amino acid sequence of an example of the enzyme encoded by the hyperthermostable protease gene obtained by the present invention. In the DNA fragment inserted into the plasmid pTC3, the sequence derived from lambda GEM-11 vector is adjacent to the 5'-end of the nucleotide sequence represented by SEQ ID NO 7 of the Sequence Listing, indicating a defect in a part of the 5'-region of the protease gene. In addition, by comparing the nucleotide sequence with those of SEQ ID NO 10 and 11 of the Sequence Listing, it has been found that the DNA fragment inserted into the plasmid pTC3 contains the 41st and the subsequent nucleotides of the nucleotide sequence represented by SEQ ID NO 10 and the whole nucleotide sequence of SEQ ID NO 11.

Although the hyperthermostable protease gene obtained from *Thermococcus celer* is defect in a part thereof, as is obvious to a person skilled in the art, a DNA fragment containing the whole length of the hyperthermostable protease gene can be obtained, for example, (1) by repeating screening of a genomic DNA library, (2) by carrying out Southern hybridization with genomic DNA, (3) by obtaining a DNA fragment of the 5'-upstream region by PCR with a cassette (manufactured by Takara Shuzo Co., Ltd.) and cassette primers (manufactured by Takara Shuzo Co., Ltd.) (Takara Shuzo's Genetic Engineering Products Guide, 1994–1995 ed., pp. 250–251), and the like.

A transformant into which a recombinant plasmid containing with the hyperthermostable protease gene is transduced, for example, *Escherichia coli* JM109/pTPR13 or *Escherichia coli* JM109/pTPR36, can be cultured under conventional conditions, for example, by culturing the transformant in LB medium [trypton (10 g/liter), yeast extract (5 g/liter), NaCl (5 g/liter); pH 7.2] containing 100 μg/ml of ampicillin at 37° C. to express the hyperthermostable protease in the culture. After completion of culture, the cultured cells are harvested and the cells are sonicated and centrifuged. The supernatant is subjected to heat treatment at 100° C. for 5 minutes to denature and remove contaminated proteins. In this way, a crude enzyme sample can be obtained. The crude enzyme samples thus obtained from *Escherichia coli* JM109/pTPR13 and *Escherichia coli* JM109/pTPR36 have been named as PF-13 and PF-36.

Further, a transformant into which a recombinant plasmid containing the hyperthermostable protease gene is transduced, *Bacillus subtilis* DB104/pUBP13, can be cultured under conventional conditions, for example, by culturing the transformant in LB medium containing 10 μg/ml of kanamycin at 37° C. to express the hyperthermostable protease in the culture. After completion of culture, the cultured cells are harvested and the cells are sonicated and centrifuged. The supernatant is subjected to heat treatment at 100° C. for 5 minutes to denature and remove contaminated proteins, followed by salting out with ammonium sulfate and dialysis. In this way, a partially purified enzyme sample can be obtained. The roughly purified enzyme sample thus obtained from *Bacillus subtilis* DB104/pUBP13 has been named as PF-BS13.

The enzymatic and physicochemical properties of the hyperthermostable protease samples produced by the transformants into which the recombinant plasmids containing the hyperthermostable protease genes derived from *Pyrococcus furiosus* obtained by the present invention, for example, PF-13, PF-36 and PF-BS13 are as follows.

(1) Activity

The enzymes obtained by the present invention hydrolyze gelatin to form short chain polypeptides. In addition, they hydrolyze casein to form short chain polypeptides.

(2) Method for detecting enzyme activity The detection of enzyme activity was carried out by detection of hydrolysis of gelatin with the enzyme on a SDS-polyacrylamide gel. Namely, an enzyme sample to be tested was suitably diluted and to 10 μl of the sample diluted solution was added 2.5 μl of a sample buffer solution (50 mM Tris-HCl pH 7.6, 5% SDS, 5% 2-mercaptoethanol, 0.005% Bromophenol Blue, 50% glycerol). The mixture was subjected to heat treatment at 100° C. for 5 minutes and then electrophoresis by using 0.1% SDS-10% polyacrylamide gel containing 0.05% gelatin. After completion of electrophoresis, the gel was soaked in 50 mM potassium phosphate buffer (pH 7.0) and incubated at 95° C. for 2 hours to carry out the enzymatic reaction. Then, the gel was stained with 2.5% Coomassie Brilliant Blue R-250 in 25% ethanol and 10% acetic acid for 30 minutes and further the gel was transferred in 25% ethanol and 7% acetic acid to remove excess dye over 3 to 15 hours. Gelatin hydrolyzed with the protease into peptides was diffused outside of the gel during the enzymatic reaction and the corresponding position was not stained with Coomassie Brilliant Blue, thereby detecting the presence of the protease activity. The enzyme samples obtained by the present invention, PF-13, PF-36 and PF-BS13, had gelatin hydrolyzing activity at 95° C.

In addition, the casein hydrolyzing activity was detected according to the same manner as described above except that a 0.1% SDS-10% polyacrylamide gel containing 0.05% of casein was used. The enzyme samples obtained by the present invention, PF-13, PF-36 and PF-BS13, had casein hydrolyzing activity at 95° C.

Moreover, casein hydrolyzing activity of the enzyme sample obtained by the present invention, PF-BS13, was determined by the following method. To 100 μl of 0.1M potassium phosphate buffer (pH 7.0) containing 0.2% casein was added 100 μl of a suitably diluted enzyme solution and incubated at 95° C. for 1 hour. The reaction was stopped by addition of 100 μl of 15% trichloroacetic acid and the reaction mixture was centrifuged. The amount of acid soluble short chain polypeptides contained in the supernatant was determined by measuring absorbance at 280 nm and the enzyme activity was determined by comparing the absorbance with that of an enzyme free control. The enzyme sample obtained by the present invention, PF-BS13, had casein hydrolyzing activity under the experimental conditions of pH 7.0 at 95° C.

(3) Stability Stability of the enzyme was examined by detecting remaining enzymatic activity of heat treated enzymes by the above-described method (2) using SDS-polyacrylamide gel containing gelatin. Namely, the enzyme sample was incubated at 95° C. for 3 hours and then a suitable amount thereof was subjected to detection of the enzymatic activity to compare its activity with that without treatment at 95° C. Although the position of enzyme activity on the gel was somewhat changed due to incubation at 95° C., lowering of the enzyme activity was scarcely observed. The enzyme samples obtained by the present invention, PF-13, PF-36 and PF-BS13, were stable to heat treatment at 95° C. for 3 hours.

In addition, stability of the enzyme samples obtained by the present invention, PF-13 and PF-36, in the presence of surfactants were tested. Namely, Triton X-100, SDS or benzalkonium chloride was added to the enzyme samples in the final concentration of 0.1%. The mixture was incubated at 95° C. for 3 hours and a suitable amount thereof was subjected to detection of the enzymatic activity. For each surfactant, no substantial change in the enzyme activity was found in comparison with that in the absence of the surfactant. Then, the enzyme samples obtained by the present invention, PF-13 and PF 36, were stable to heat treatment at 95° C. for 3 hours in the presence of surfactants.

Figure 16:
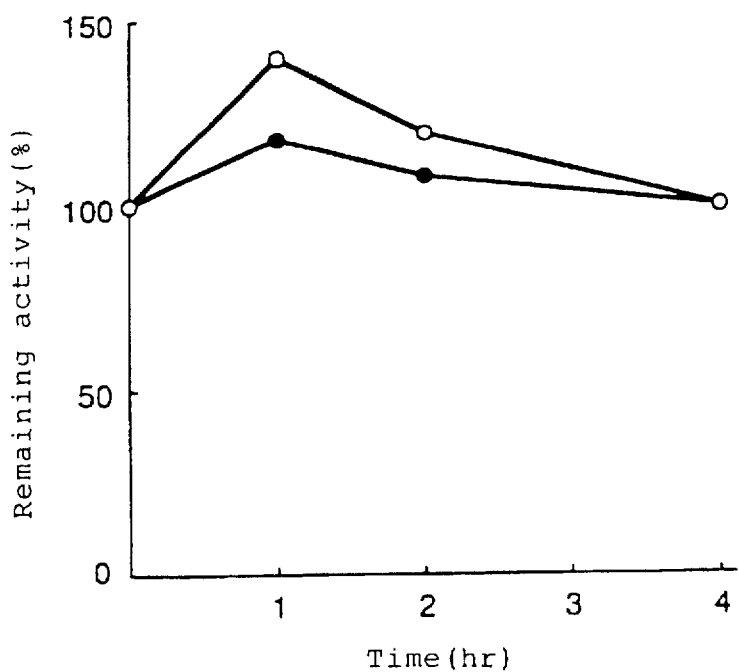
FIG. 16 illustrates thermostability of the hyperthermostable protease obtained in the present invention.

Moreover, stability of the enzyme sample obtained by the present invention, PF-BS13, was tested by the following method. Namely, the enzyme sample as such or with addition of SDS in the final concentration of 0.1% was incubated at 95° C. for various periods of time and the remaining activity was determined by the above-described spectrophotometric method (2) based on increase in the amount of acid soluble polypeptides. FIG. 16 illustrates thermostability of the enzyme sample obtained by the present invention, PF-BS13. The ordinate indicates the remaining activity (%) and the abscissa indicates incubation time (hr). In FIG. 16, the open circle represents the results obtained without addition of SDS and the closed circle represents the results in the presence of 0.1% SDS. As seen from FIG. 16, PF-BS13 maintained almost 100% activity after incubation at 95° C. for 4 hours regardless of the presence or absence of 0.1% SDS.

(4) Effect of various reagents

The enzyme samples were subjected to SDS-polyacrylamide gel containing gelatin and then the enzymatic reaction was carried out in 50 mM potassium phosphate buffer (pH 7.0) containing 2 mM EDTA or 2 mM phenylmethanesulfonyl fluoride (PMSF) to test for effect of both reagents on the enzyme activity. No substantial difference in the enzyme activities of the enzyme samples obtained by the present invention, PF-13, PF-36 and PF-BS13, was observed between the buffer containing 2 mM EDTA and 50 mM potassium phosphate buffer alone. On the other hand, when the buffer containing 2 mM PMSF was used, the amount of hydrolyzed gelatin in the gel was decreased in all the samples, indicating that the activities of the enzyme samples were inhibited by PMSF.

(5) Molecular weight

The molecular weight of the enzyme sample obtained by the present invention on a SDS-polyacrylamide gel containing ing gelatin was estimated. The enzyme sample, PF-13, showed plural active bands within the range of 95 kDa to 51 kDa. Although the migration distance was varied according to the amount of a sample applied, etc., the major bands of 84 kDa, 79 kDa, 66 kDa, 54 kDa and 51 kDa were appeared. When the enzyme sample was subjected to electrophoresis after heat treatment at 95° C. for 3 hours in the presence of SDS in the final concentration of 0.1%, the bands of 63 kDa and 51 kDa became intensive. For the enzyme sample, PF-BS13, the same results as that of the above with respect to the enzyme sample PF-13 were obtained. In case of the enzyme sample PF-36, several minor bands were observed in addition to the main bands of 63 kDa and 59 kDa.

(6) Optimum pH

The optimum pH of the enzyme samples PF-13 and PF-36 obtained by the present invention was tested. After subjecting the enzyme samples to electrophoresis on a SDS-polyacrylamide gel containing gelatin, the gel was soaked in buffers having different pH and the enzyme reaction was carried out to test for the optimum pH. As the buffers, 50 mM sodium acetate buffer solution at pH 4.0 to 6.0, 50 mM potassium phosphate buffer solution at pH 6.0 to 8.0, 50 mM sodium borate buffer solution at pH 9.0 to 10.0 were used. Both enzyme samples showed gelatin hydrolyzing activity at pH 6.0 to 10.0 and their optimum pH was pH 8.0 to 9.0.

Figure 17:
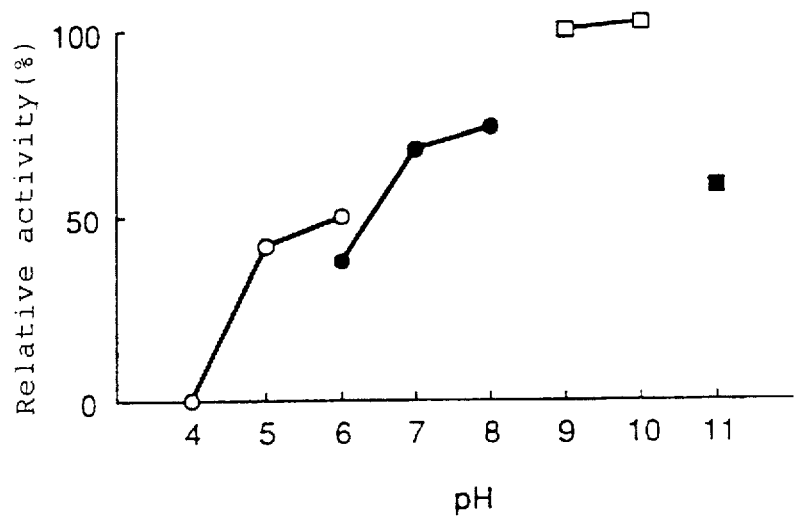
FIG. 17 illustrates the optimum pH of the hyperthermostable protease obtained in the present invention.

In addition, the optimum pH of the enzyme sample obtained by the present invention, PF-BS13, was determined by the above-described spectrophotometric method (2) based on increase in the amount of acid soluble polypeptides. 0.2% Casein solutions to be used for the determination were prepared by using 0.1M sodium acetate butter solution at pH 4.0 to 6.0, 0.1M potassium phosphate buffer solution at pH 6.0 to 8.0, 0.1M sodium borate buffer solution at pH 9.0 to 10.0 and 0.1M sodium phosphate-sodium hydroxide buffer solution at pH 11.0 and they were used for the determination. FIG. 17 illustrates the relation between casein hydrolyzing activity of the enzyme sample obtained by the present invention, PF-BS13 and pH. The ordinate indicates the relative activity (%) and the abscissa indicates pH. In Fig. 17, the open circle, the closed circle, the open square and the closed square represent the results obtained by using the substrate solutions prepared with 0.1M sodium acetate buffer solution, 0.1M potassium phosphate buffer solution, 0.1M sodium borate buffer solution and 0.1M sodium phosphate-sodeum hydroxide, respectively. As seen from FIG. 17, the enzyme sample, PF-BS13, showed casein decomposing activity at the pH range of 5.0 to 11.0 and its optimum pH was pH 9.0 to 10.0.

As described hereinabove in detail, according to the present invention, the genes encoding the hyperthermostable proteases and the industrial process for producing the hyperthermostable proteases using the genes can be provided. The enzymes have high thermostability and also show resistance to surfactants. Therefore, they are particularly useful for treatment of proteins at high temperatures.

In addition, a DNA fragment obtained by hybridization with the gene isolated by the present invention or a part of the nucleotide sequence of the isolated gene as a probe can be transduced into a suitable microorganism and its heat-treated lysate can be prepared according to the same manner as that described with respect to the cosmid protein library. Then, a protease activity is tested by an appropriate method. In this manner, a hyperthermostable protease gene encoding an enzyme whose sequence is not identical with that of the above enzyme but which has a similar activity can be obtained.

The above hybridization can be carried out under the following conditions. Namely, DNA fixed on a membrane is incubated in 6×SSC containing 0.5% of SDS, 0.1% of bovine serum albumin, 0.1% of polyvinyl pyrrolidone, 0.1% of Ficoll 400 and 0.01% denatured salmon sperm DNA (1×SSC represents 0.15M NaCl and 0.015M sodium citrate, pH 7.0) together with a probe at 50° C. for 12 to 20 hours. After completion of incubation, the membrane is washed in such a manner that washing is started with 2×SSC containing 0.5% SDS at 37° C., followed by changing SSC concentrations within the range to 0.1×and varying temperatures up to 50° C., until a signal from the fixed DNA can be distinguished from the background signal.

Furthermore, the gene isolated by the present invention, a DNA fragment obtained by in vitro gene amplification using a part of the isolated gene as a primer, or a DNA fragment obtained by hybridization using the fragment obtained by the above amplification as a probe is transduced into a suitable microorganism and, according to the same manner as described above, a protease activity is determined. In this manner, a hyperthermostable protease gene encoding an enzyme whose activity is not identical with that of the above enzyme but is similar can be obtained.

The following examples further illustrates the present invention but are not to be construed to limit the scope thereof. In the examples, all the "percents" are by weight.

EXAMPLE 1

Preparation of genomic DNA of *Pyrococcus furiosus*

*Pyrococcus furiosus* DSM3638 was cultured as follows.

A culture medium composed of 1% of trypton, 0.5% of yeast extract, 1% of soluble starch, 3.5% of Jamarin S·Solid (manufactured by Jamarin Laboratory), 0.5% of Jamarin S·Liquid (manufactured by Jamarin Laboratory), 0.003% of $MgSO_4$, 0.001% of NaCl, 0.0001% of $FeSO_4 \cdot 7H_2O$, 0.0001% of $COSO_4$, 0.0001% of $CaCl_2 \cdot 7H_2O$, 0.0001% of $ZnSO_4$, 0.1 ppm of $CuSO_4 \cdot 5H_2O$, 0.1 ppm of $KAl\,(SO_4)_2$, 0.1 ppm of $H_3BO_3$, 0.1 ppm of $Na_2MoO_4 \cdot 2H_2O$ and 0.25 ppm of $NiCl_2 \cdot 6H_2O$ was placed in a 2 liter-medium bottle and sterilized at 120° C. for 20 minutes. Then, nitrogen gas was blown into the medium to purge out dissolved oxygen and the above bacterial strain was inoculated into the medium, followed by subjecting to stationary culture at 95° C. for 16 hours. After completion of culture, bacterial cells were collected by centrifugation.

Then, the collected cells were suspended into 4 ml of 0.05M Tris-HCl (pH 8.0) containing 25% of sucrose and to this suspension were added 0.8 ml of lysozyme [5 mg/ml, 0.25M Tris-HCl (pH 8.0)] and 2 ml of 0.2M EDTA. The mixture was incubated at 20° C. for 1 hour. Then, to the mixture were added 24 ml of SET solution [150 mM NaCl, 1 mM EDTA and 20 mM Tris-HCl (pH 8.0)] and further 4 ml of 5% SDS and 400 μl of Proteinase K (10 mg/ml) and the mixture was incubated at 37° C. for 1 hour. After completion of the reaction, the reaction mixture was subjected to phenol-chloroform extraction and then ethanol precipitation to prepare about 3.2 mg of genomic DNA.

Preparation of cosmid protein library 400 μg of Genomic DNA of *Pyrococcus furiosus* DSM3633 was partially digested with Sau3AI and subjected to size-fractionation in size of 35 to 50 kb by density-gradient ultra-centrifugation. Then, 1 μg of a triple helix cosmid vector was digested with XbaI, dephosphorylated with alkaline phosphatase (manufactured by Takara Shuzo Co., Ltd.) and further digested with BamHI. The vector was ligated to 140 μg of the above fractionated 35 to 50 kb DNA. The genomic DNA fragments of *Pyrococcus furiosus* were packaged into lambda phage particles by in vitro packaging method using Gigapack Gold (manufactured by Stratagene) to prepare a library. Then, by using a part of the library thus obtained, transduction into *E. coli* DH5αMCR was carried out and, among transformants obtained, several transformants were selected to prepare cosmid DNA. After confirmation of the presence of inserted fractions having suitable size, again about 500 transformants were selected from the above library and they were independently cultured in 150 ml of LB medium (tripton 10 g/liter, yeast extract 5 g/liter, NaCl 5 g/liter, pH 7.2) containing 100 μg/ml of ampicillin. Each culture was centrifuged, the recovered microbial cells were suspended in 1 ml of 20 mM Tris-HCl (pH 8.0) and the suspension was subjected to heat treatment at 100° C. for 10 minutes. Then, the suspension was sonicated and again subjected heat treatment at 100° C. for 10 minutes. The lysates obtained as supernatants after centrifugation were used as the cosmid protein library.

Selection of cosmid containing hyperthermostable protease gene

The protease activity was detected by testing for hydrolysis gelatin in a polyacrylamide gel.

Namely, 5 μl aliquots of the lysates from the above cosmid protein library were taken out and subjected to electrophoresis by using 0.1% SDS-10% polyacrylamide gel containing 0.05% of gelatin. After completion of electrophoresos, the gel was incubated in 50 mM potassium phosphate buffer solution (pH 7.0) at 95° C. for 2 hours. The gel was stained in 2.5% Coomassie Brilliant Blue-R-250, 25% ethanol and 10% acetic acid for 30 minutes. Then, the gel was transferred to 25% methanol and 7% acetic acid to decolorize for 3 to 15 hours. Eight cosmid clones having the protease activity, which shows the bands not stained with Coomassie Brilliant Blue-R-250 due to hydrolysis of gelatin on the gel were selected.

Preparation of plasmid pTPR1 containing hyperthermostable protease gene

Among the 8 cosmid clones having the protease activity, one cosmid (cosmid No. 304) was selected to prepare cosmid DNA and the cosmid DNA was digested with SphI and then ligated to SphI site of the plasmid vector pUC119. This recombinant plasmids were transduced into *E. coli* JM109 and the protease activity of the resultant transformants were tested according to the same method as that used for screening of the cosmid protein library. A plasmid was prepared from the transformant having the protease activity and the resultant recombinant plasmid was named as pTPR1. *E. coli* JM109 transformed with the plasmid was named as *Escherichia* JM109/pTPR1.

FIG. 1 illustrates a restriction map of the plasmid pTPR1.

Preparation of plasmid pTPR9 containing hyperthermostable protease gene

The above plasmid pTPR1 was digested with XbaI and subjected to agarose gel-electrophoresis to separate three DNA fragments of about 2.5 kb, about 3.3 kb and about 4.3 kb. Among three fragments thus separated, two fragments of about 3.3 kb and about 4.3 kb were recovered. The DNA fragment of about 4.3 kb was dephosphorylated with alkaline phosphatase (manufactured by Takara Shuzo Co., Ltd.) and then was mixed with the DNA fragment of about 3.3 kb to ligate to each other. This was transduced into *E. coli* JM109. The protease activity of the resultant transformants were tested by the same method as that used for screening of the cosmid protein library. A plasmid was prepared from the transformant having the protease activity. The plasmid was named as pTPR 9 and *E. coli* JM109 transformed with the plasmid was named as *Escherichia coli* JM109/pTPR9.

FIG. 2 illustrates a restriction map of the plasmid pTPR 9.

Detection of DNA fragment containing whole length of hyperthermostable protease gene The cosmid DNA used in the preparation of the above plasmid pTPR1 was digested with NotI and then further digested with BamHI, BlnI, EcoT22, Nsp(7524)V, PvuII, SalI, SmaI and SpeI, respectively. Then, digested DNA was subjected to electrophoresis on a 0.8% agarose gel. After electrophoresis, the gel was soaked in 0.5N NaOH containing 1.5M NaCl to denature the DNA fragments in the gel and then the gel was neutralized in 0.5M Tris-HCl (pH 7.5) containing 3M NaCl. The DNA fragments in the gel was blotted on a Hybond-N$^+$ nylon membrane (manufactured by Amasham) by Southern blotting. After blotting, the membrane was washed with 6×SSC (1×SSC represents 0.15M NaCl, 0.015M sodium citrate, pH 7.0) and air-dried and DNA was fixed on the membrane by UV irradiation using a UV transilluminator for 3 minutes.

On the other hand, the plasmid pTPR9 was digested with PstI and XbaI and subjected to electrophoresis on a 1% agarose gel and the separated DNA fragment of about 0.7 kb was recovered. A $^{32}$P-labeled DNA probe was prepared by using the DNA fragment as a template and using a random primer DNA labeling kit Ver2 (manufactured by Takara Shuzo Co., Ltd.) and [α-$^{32}$P]dCTP (manufactured by Amasham).

The above membrane to which the DNA was fixed was treated in a hybridization buffer solution (6×SCC containing 0.5% SDS, 0.1% bovine serum albumin, 0.1% polyvinyl pyrrolidone, 0.1% Ficoll 400 and 0.01% denatured salmon sperm) at 68° C. for 2 hours. Then, it was transferred in a similar hybridization buffer solution containing the $^{32}$P-labeled DNA probe to allow to hybridize at 68° C. for 14 hours. After completion of hybridization, the membrane was washed with 2×SSC containing 0.5% of SDS at room temperature and then 0.1×SSC containing 0.5% of SDS at 68° C. After rinsing the membrane with 0.1×SSC, it was air-dried. A X-ray film was exposed to the membrane at –80° C. for 60 hours. The film was developed to prepare an autoradiogram. This autoradiogram showed that a protease gene was present in the DNA fragment of about 7.5 kb obtained by digestion of the cosmid DNA with NotI and PvuII.

Preparation of plasmid pTPR12 containing whole length of hyperthermostable protease gene The cosmid DNA used for the preparation of the above plasmid pTPR1 was digested with Not I and PvuII and subjected to electrophoresis using a 0.8% agarose gel to recover DNA fragments of about 7 to 8 kb all together. These DNA fragments were mixed with the plasmid vector pUC19 into which a Not I linker was introduced at HincII site and which was digested with NotI and SmaI. Then, ligation was carried out. The recombinant plasmids were transduced into *E. coli* JM109 and the protease activity of the resultant transformants were tested by the same method as that used for screening of the cosmid protein library. A plasmid was prepared from the transformant having the protease activity. The plasmid was named as pTPR12 and *E. coli* JM109 transformed with the plasmid was designated as *Escherichia coli* JM109/pTPR12.

FIG. 3 illustrates a restriction map of the plasmid pTPR12.

Preparation of plasmid pTPR 15 containing whole length of hyperthermostable protease gene The above plasmid pTPR 12 was digested with XbaI and subjected to electrophoresis using a 1% agarose gel to recover separated two DNA fragments of about 3.3 kb and about 7 kb, respectively. Then, the DNA fragments of about 7 kb thus recovered was digested with KpnI and again subjected to electrophoresis using a 1% agarose gel to separate two fragments of about 3.2 kb and about 3.8 kb. In these fragments, the DNA fragment of about 3.2 kb was recovered and ligated to the plasmid vector pUC19 digested with XbaI and KpnI. This was transduced into *E. coli* JM109. Plasmids held by the resultant transformants were prepared and the plasmid containing only one molecular of the above 3.2 kb fragment was selected. This was named as pTPR14.

FIG. 5 illustrates a restriction map of the plasmid pTPR 14.

Then, the above plasmid pTPR 14 was digested with XbaI and dephosphorylated using alkaline phosphatase. This was mixed with the above fragment of about 3.3 kb to carry out ligation and was transduced into *E. coli* JM109. The protease activity of the resultant transformants were tested by using the same method as that used for screening of the cosmid protein library. A plasmid was prepared from the transformant having the protease activity. This plasmid was named as pTPR15 and *E. coli* JM109 transformed with the plasmid was named as *Escherichia coli* JM109/pTPR15.

FIG. 6 illustrates a restriction map of the plasmid pTPR 15.

EXAMPLE 2

Determination of nucleotide sequence of hyperthermostable protease gene

For determination of the nucleotide sequence of the hyperthermostable protease gene inserted into the above plasmid pTPR 15, deletion mutants wherein the DNA fragment portion inserted into the plasmid had been deleted in various lengths were prepared by using Kilo sequence deletion kit (manufactured by Takara Shuzo Co., Ltd.). Among them, several mutants having suitable lengths of deletion were selected and nucleotide sequences of respective inserted DNA fragment portions were determined by dideoxy method using BcaBEST dideoxy sequencing kit (manufactured by Takara Shuzo Co., Ltd.). By putting these results together, nucleotide sequences of the inserted DNA fragment contained in the plasmid pTPR15 were determined. Among the nucleotide sequences thus obtained, SEQ ID NO 8 of the Sequence Listing shows the fragment of 4765 bp between two DraI sites. Furthermore, SEQ ID NO 9 shows an amino acid sequence of the hyperthermostable protease encoded by the open reading frame contained in the above nucleotide sequence.

Preparation of plasmid pTPR13 containing hyperthermostable protease gene

The above plasmid pTPR15 was digested with DraI and subjected to 1% agarose gel-electrophoresis, followed by recovering the separated DNA fragment of about 4.8 kb. Then, the plasmid vector pUC19 was digested with SmaI and, after dephosphorylation with alkaline phosphatase, it was mixed with the above DNA fragment of about 4.8 kb to carry out ligation and transduced into *E. coli* JM109. The protease activity of the resultant transformants were tested by the same method as that used for screening of the cosmid protein library. A plasmid was prepared from a transformant having the activity. The plasmid was named as pTPR13 and *E. coli* JM109 transformed with the plasmid was named as *Escherichia coli* JM109/pTPR13.

FIG. 7 illustrates a restriction map of the plasmid pTPR13.

Preparation of plasmid pUBP13 containing hyperthermostable protease gene for transforming *Bacillus subtilis*

The above plasmid pTPR13 was digested with KpnI and BamHI and then subjected to 1% agarose gel-electrophoresis, followed by recovering the separated DNA fragment of about 4.8 kb. Then, the plasmid vector pUB18-P43 was digested with KpnI and BamHI and mixed with the above DNA fragment of about 4.8 kb to carry out ligation. It was transduced into *Bacillus subtilis* DB104. The protease activity of the resultant transformants having kanamycin resistance were tested by the same method as that used for screening of the cosmid protein library. A plasmid was prepared from a transformant having the activity. The plasmid was named as pUBP13 and *Bacillus subtilis* DB104 transformed with the plasmid was named as *Bacillus subtilis* DB1049/pUBP13.

FIG. 8 illustrates a restriction map of the plasmid pUBP13.

Preparation of plasmid pTPR36 containing hyperthermostable protease gene defecting in its back half portion The above plasmid pTPR13 was digested with EcoRI and the resultant end was blunted with a DNA blunting kit (manufactured by Takara Shuzo Co., Ltd.). Further, it was digested with KpnI and subjected to 1% agarose gel-electrophoresis, followed by recovering the separated DNA fragment of about 2.8 kb. Next, the plasmid vector pUC119 was digested with XbaI and the resultant end was blunted and further digested with KpnI, followed by mixing with the above DNA fragment of 2.8 kb to carry out ligation and transducing into *E. coli* JM109.

The protease activity of the resultant transformants were tested by the same method as that used for screening of the cosmid protein library. A plasmid was prepared from a transformant having the activity. The plasmid was named as pTPR36 and *E. coli* JM109 transformed with the plasmid was named as *Escherichia coli* JM109/pTPR36.

FIG. 9 illustrates a restriction map of the plasmid pTPR36. SEQ ID NO 2 of the Sequence Listing shows the nucleotide sequence of the DNA fragment inserted into the plasmid pTPR36. Also, SEQ ID NO 1 shows an amino acid sequence of the hyperthermostable protease which can be encoded by the nucleotide sequence.

EXAMPLE 3

Preparation of oligonucleotide for detection of hyperthermostable protease gene

By comparing the estimated amino acid sequence of the hyperthermostable protease of the present invention obtained in Example 2 with amino acid sequences of known alkaline serine proteases originating in microorganisms, it was found that there were homologous amino acid sequences commonly present in these enzymes. Among them, three regions were selected and oligonucleotides to be used as primers in detection of hyperthermostable protease genes by PCR were designed.

FIGS. 10, 11 and 12 illustrate the relation among the amino acid sequences corresponding to the above three regions of the hyperthermostable protease of the present invention, nucleotide sequences of the hyperthermostable protease of the present invention which encode the above regions, and the nucleotide sequences of oligonucleotides PRO-1F, PRO-2F, PRO-2R and PRO-4R synthesized based on the above nucleotide sequences. Also, SEQ NO. 3, 4, 5 and 6 show nucleotide sequences of PRO-1F, PRO-2F, PRO-2R and PRO-4R, respectively.

Preparation of genomic DNA of *Thermococcus celer*

Microbial cells were collected from 10 ml of a culture broth of *Thermococcus celer* DSM2476 obtained from Deutsch Sammlung von Microorganismen und Zellkulturen GmbH by centrifugation and suspended in 100 μl of 50 mM Tris-HCl (pH 8.0) containing 25% sucrose. To the suspension were added 20 μl of 0.5M EDTA and 10 μl of lysozyme (10 mg/ml) and the suspension was incubated at 20° C. for 1 hour. To this were added 800 μl of SET solution (150 mM NaCl, 1 mM EDTA, 20 mM Tris-HCl, pH 8.0), 50 μl of 10% SDS and 10 μl of Proteinase K (20 mg/ml) and the suspension was further incubated at 37° C. for 1 hour. Chloroform-phenol extraction was carried out to stop the reaction. The reaction mixture was subjected to ethanol precipitation and recovered DNA was dissolved in 50 μl of TE buffer solution to obtained a genomic DNA solution.

Detection of hyperthermostable protease by PCR

A PCR reaction mixture was prepared from the above genomic DNA of *Thermococcus celer* and the oligonucleotides PRO-1F and PRO-2R or the oligonucleotides PRO-2F and PRO-4R and a PCR reaction (one cycle: 94° C. for 1 minute–55° C. for 1 minute–72° C. for 1 minute, 35 cycles) was carried out. When aliquots of the reaction mixture were subjected to agarose gel-electrophoresis, amplification of three DNA fragments in case of using the oligonucleotides PRO-1F and PRO-2R and one DNA fragment in case of using the oligonucleotides PRO-2F and PRO-4R was observed. These amplified fragments were recovered from the agarose gel and their DNA ends were blunted by a DNA blunting kit, followed by phosphorylating thereof with T4 polynucleotide kinase (manufactured by Takara Shuzo Co., Ltd.). Then, the plasmid vector pUC18 was digested with HincII and subjected to dephosphorylation with alkaline phosphatase. It was mixed with the above PCR amplified DNA fragments to carry out ligation and then transduced into *E. coli* JM109. Plasmids were prepared from the resultant transformants and plasmids into which suitable DNA fragments were inserted were selected. Nucleotide sequences of the inserted DNA fragments were determined by dideoxy method. Among these plasmids, regarding a plasmid p1F-2R(2) containing a DNA fragment of about 150 bp which was amplified by using the oligonucleotides PRO-1F and PRO-2R and a plasmid p2F-4R containing a DNA fragment of about 550 bp which was amplified by using the oligonucleotides PRO-2F and PRO-4R, it was found that amino acid sequences estimated from the thus-obtained nucleotide sequences contained sequences having homology with the amino acid sequences of the hyperthermostable protease originating in *Pyrococcus furiosus* of the present invention, subtilisin and the like.

SEQ NO 10 of the Sequence Listing shows the nucleotide sequence of the DNA fragment inserted into the plasmid p1F-2R(2) and an amino acid sequence deduced from the nucleotide sequence. Also, SEQ NO 11 of the Sequence Listing shows the nucleotide sequence of the DNA fragment inserted into the plasmid p2F-4R and an amino acid sequence deduced from the nucleotide sequence. In the nucleotide sequence shown by SEQ NO 10 of the Sequence Listing, the sequence from the first to 21st nucleotides and that from the 113th to 145th nucleotides and, in the SEQ NO 11 of the Sequence Listing, the sequence from the first to the 32nd nucleotides and that from the 532nd to the 564th nucleotides are the sequences of the primers used in the PCR (corresponding to the oligonucleotides PRO-1F, PRO-2R, PRO-2F and PRO-4R, respectively).

FIG. 13 illustrates a restriction map of the plasmid p2F-4R.

Screening of protease gene originating in *Thermococcus celer*

The above genomic DNA of *Thermococcus celer* was partially digested with Sau3AI and was treated with Klenow fragment (manufactured by Takara Shuzo Co., Ltd.) in the presence of dATP and dGTP to partially repair the DNA ends. The DNA fragments were mixed with a lambda GEM-11 XhoI half site arm vector (manufactured by Promega) to carry out ligation. Then, they were subjected to in vitro packaging using Gigapack Gold to prepare a lambda phage library containing genomic DNA of *Thermococcus celer*. A part of the library was transduced into *E. coli* LE392 to form plaques on a plate and the plaques were transferred on a Hybond-N⁺-membrane. After transfer, the membrane was treated with 0.5 N NaOH containing 1.5M NaCl and then 0.5M Tris-HCl (pH 7.5) containing 3M NaCl. Further, it was washed with 6×SCC, air-dried and irradiated with UV light on a UV transilluminator to fix phage DNA on the membrane.

On the other hand, the plasmid p2F-4R was digested with PmaCI (manufactured by Takara Shuzo Co., Ltd.) and StuI (manufactured by Takara Shuzo Co., Ltd.) and subjected to 1% agarose gel-electrophoresis to recover the separated DNA fragment of about 0.5 kb. By using this fragment as a template and using a random primer DNA labeling kit Ver2 and [α-$^{32}$P]dCTP, a $^{32}$P-labeled DNA probe was prepared.

The above membrane having DNA fixed thereon was treated in a hybridization buffer solution (6×SSC containing 0.5% SDS, 0.1% bovine serum albumin, 0.1% polyvinyl pyrrolidone, 0.1% Ficoll 400 and 0.01% denatured salmon sperm DNA) at 50° C. for 2 hours. It was transferred to the same buffer solution containing the $^{32}$P-labeled DNA prove and hybridization was carried out at 50° C. for 15 hours. After completion of hybridization, the membrane was washed with 2×SSC containing 0.5% SDS at room temperature and then 1×SSC containing 0.5% SDS at 50° C. Further, after rinsing the membrane with 1×SCC, it was air-dried and a X-ray film was exposed thereto at −80° C. for 6 hours to prepare an autoradiogram. About 4,000 phage clones were screened. As a result, one phage clone containing a protease gene was obtained. Based on the signal on the autoradiogram, the position of this phage clone was found and the plaque corresponding on the plate used for transfer to the membrane was isolated into 1 ml of SM buffer solution [50 mM Tris-HCl, 0.1M NaCl, 8 mM MgSO₄, 0.01% gelatin (pH 7.5)] containing 1% of chloroform.

Detection of phage DNA fragment containing protease gene

The above phage clone was transduced in to *E. coli* LE392 and the transformant was cultured in NZCYM medium (manufactured by Bio 101) at 37° C. for 15 hours to obtain a culture broth. A supernatant of the culture broth was collected and phage DNA was prepared by using QIAGEN-lambda kit (manufactured by DIAGEN). The resultant phage DNA was digested with BamHI, EcoRI, EcoRV, HincII, KpnI, NcoI, PstI, SacI, SalI, SmaI and SphI (all manufactured by Takara Shuzo Co., Ltd.), respectively, and subjected to 1% agarose-electro-phoresis. Then, a membrane on which DNA fragments were fixed was prepared by the same method as that used for the detection of the DNA fragment containing the whole length of the hyperthermostable protease gene of Example 1. The membrane was treated in a hybridization buffer solution at 50° C. for 4 hours and then transferred to the same hybridization buffer solution containing the same $^{32}$P-labeled DNA probe as that used in the above screening of the protease gene derived form *Thermococcus celer*. Then, hybridization was carried out at 50° C. for 18 hours. After completion of hybridization, the membrane was washed with 1×SSC containing 0.5% SDS at 50° C. and rinsed with 1×SCC. The membrane was air-dried and exposed to a X-ray film at −80° C. for 2 hours to prepare an autoradiogram. According to this autoradiogram, it was found that, in the phage DNA digested with KpnI, the protease gene was contain in a DNA fragment of about 9 kb.

Preparation of plasmid pTC1 containing protease gene

The above phage DNA containing the protease gene was digested with KpnI and subjected to 1% agarose gel-electrophoresis to recover a DNA fragment of about 9 kb from the gel. Then, the plasmid vector pUC119 was digested with KpnI and dephosphorylated with alkaline phosphatase, followed by mixing with the above DNA fragment of about 9 kb to carry out ligation. Then, it was transduced into *E. coli* JM109. Plasmids were prepared from the resultant transformants and a plasmid containing only the above DNA fragment of about 9 kb was selected. This plasmid was named as pTC1 and *E. coli* JM109 transformed with the plasmid was named with *Escherichia coli* JM109/pTC1.

FIG. 14 illustrates a restriction map of the plasmid pTC1.

Preparation of plasmid pTC3 containing hyperthermostable protease gene

The above plasmid pTC1 was digested with KpnI and further digested with BamHI, PstI and SphI, respectively. After subjecting to 1% agarose gel-electrophoresis, according to the same operation as that for detecting the phage DNA fragment containing the above protease gene, transfer of DNA fragments to a membrane and detection of DNA fragments containing the hyperthermostable protease gene were carried out. By the signal on the resultant autoradiogram, it was shown that a DNA fragment of about 5 kb which obtained by digesting the plasmid pTC1 with KpnI and BamHI contained the hyperthermostable protease gene.

Then, the plasmid pTC1 was digested with KpnI and BamHI and then subjected to 1% agarose gel-electrophoresis to separate and isolate a DNA fragment of about 5 kb. The plasmid vector pUC119 was digested with KpnI and BamHI and mixed with the above DNA fragment of about 5 kb to carry out ligation. It was transduced into *E. coli* JM109. Plasmids were prepared form the resultant transformants and a plasmid containing the above DNA fragment of about 5 kb. This plasmid was named as pTC3 and *E. coli* JM109 transformed with the plasmid was named as *Escherichia coli* JM109/pTC3.

FIG. 15 illustrates a restriction map of the plasmid pTC3.

Determination of nucleotide sequence of hyperthermostable protease gene contained in Plasmid pTC3

For determination of the nucleotide sequence of the hyperthermostable protease gene contained in the above plasmid pTC3, 6 oligonucleotides were synthesized based on the nucleotide sequences shown by SEQ ID NO 10 and 11 of the Sequence Listing, respectively. The nucleotide sequences of the synthesized oligonucleotides TCE-2, TCE-4, SEF-3, SER-1, SER-3 and TCE-6R were shown by SEQ ID NO 12, 13, 14, 15, 16 and 17 of the Sequence Listing. The results obtained by dideoxy method using the above oligonucleotides as primers and the plasmid pTC3 as a template were summarized to determine the nucleotide sequence of the hyperthermostable protease gene.

SEQ ID NO 7 of the Sequence Listing shows a part of the resultant nucleotide sequence. In addition, SEQ ID NO 18 of the Sequence Listing shows an deduced amino acid sequence encoded by the nucleotide sequence.

EXAMPLE 4

Preparation of enzyme sample *Escherichia coli* JM109/pTPR36 which was *E. coli* JM109 into which the plasmid pTPR36 containing the hyperthermostable protease gene of the present invention obtained in Example 2 was transduced was cultured with shaking in 5 ml of LB medium (trypton 10 g/liter, yeast extract 5 g/liter, NaCl 5 g/liter, pH 7.2) containing 100 μg/ml of ampicillin at 37° C. for 14 hours. In a 1 liter-Erlenmeyer flask, 200 ml of the same medium was prepared and 2 ml of the above culture broth was inoculated and cultured with shaking at 37° C. for 10 hours. The culture broth was centrifuged. The harvested microbial cells (wet weight 1.6 g) were suspended in 2 ml of 20 mM Tris-HCl (pH 8.0), sonicated and centrifuged to obtain a supernatant. The supernatant was treated at 100° C. for 5 minutes and centrifuged again. The resultant supernatant was used as a crude enzyme solution (enzyme sample PF-36).

In addition, according to the same manner, *Escherichia coli* JM109/pTPR13 which was *E. coli* JM109 into which the plasmid pTPR13 containing the hyperthermostable protease gene of the present invention was transduced was used to prepare a crude enzyme solution (enzyme sample PF-13).

Moreover, *Bacillus subtilis* DB104/pUBP13 which was *Bacillus subtilis* DB104 into which the plasmid pUBP13 containing the hyperthermostable protease gene of the present invention was transduced was cultured with shaking in 5 ml of LB medium containing 10 μg/ml of kanamycin at 37° C. for 14 hours. In two 2 liter-Erlenmeyer flasks, respective 600 ml of the same mediums were prepared. To each flask was inoculated with 2 ml of the above culture broth and cultured with shaking at 37° C. for 26 hours. The culture broth was centrifuged. The resultant microbial cells were suspended in 15 ml of 20 mM Tris-HCl (pH 8.0), sonicated and centrifuged to obtain a supernatant. The supernatant was treated at 100° C. for 5 minutes and centrifuged again. To the resultant supernatant was added ammonium sulfate to 50% saturation and then the resultant precipitate was recovered by centrifugation. The recovered precipitate was suspended in 2 ml of 20 mM Tris-HCl (pH 8.0) and the suspension was dialyzed against the same buffer solution. The resultant inner solution was used as a partially purified enzyme sample (enzyme sample PF-BS13).

The protease activity of these enzyme samples and the cosmid clone lysate used for preparation of plasmids were tested according to the above method for detection of enzyme activity using SDS-polyacrylamide gel containing gelatin.

Figure 18:
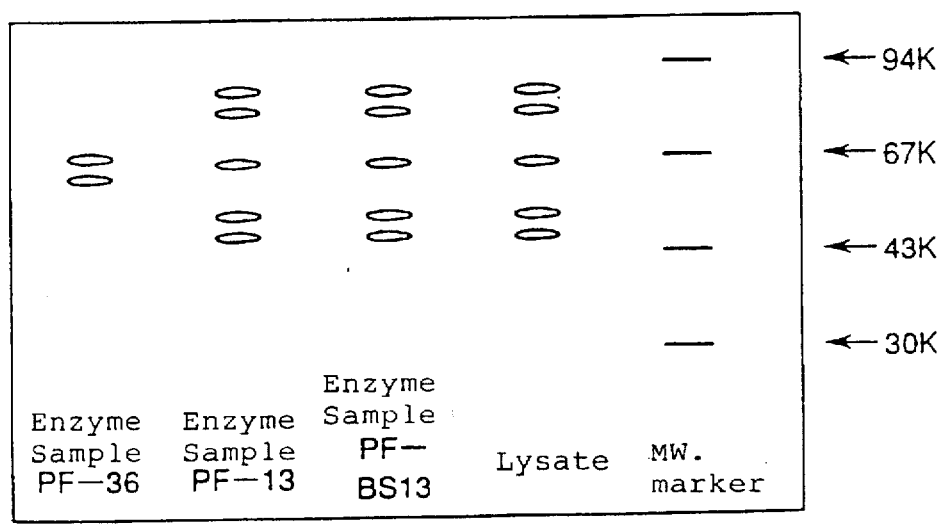
FIG. 18 illustrates the activity staining pattern after gelatin-containing SDS-polyacrylamide gel electrophoresis of the hyperthermostable protease obtained in the present invention.

FIG. 16 illustrates the thermostability of the hyperthermostable protease obtained by the present invention. And, FIG. 17 illustrates the optimum pH of the hyperthermostable protease obtained by the present invention. Further, FIG. 18 illustrates the results of activity staining after SDS-polyacrylamide gel electrophoresis of each sample (enzyme samples PF-36, PF-13 and PF-BS13 and the lysate). Each sample shows activity at 95° C. in the presence of SDS.

As described hereinabove, according to the present invention, genes encoding hyperthermostable proteases which show activity at 95° C. were obtained. These genes make possible to supply a large amount of a hyperthermostable protease having high purity.

What is claimed is:

1. An isolated hyperthermostable protease gene originating in *Pyrococcus furiosus*.

2. A hyperthermostable protease gene of claim 1 which encodes the amino acid sequence of SEQ ID NO: 1 or an enzymatically active fragment thereof.

3. A hyperthermostable protease gene of claim 1 which comprises the nucleotide sequence represented by the SEQ ID NO 2 in the Sequence Listing.

4. A hyperthermostable protease gene which is the hybridizable with the hyperthermostable protease gene of claim 2 or DNA selected from the group consisting of the nucleotide sequences represented by SEQ ID NO 3, 4, 5 and 6 in the Sequence Listing which are part of the hyperthermostable protease gene of claim 1.

5. A hyperthermostable protease gene of claim 4 which comprises the nucleotide sequence represented by the SEQ ID NO 7.

6. A process for producing a hyperthermostable protease which comprises culturing a transformant transformed with a plasmid into which the hyperthermostable protease gene of claim 1 has been transduced, and collecting the hyperthermostable protease from the culture.

7. A process for producing a hyperthermostable protease which comprises culturing a transformant transformed with a plasmid into which the hyperthermostable protease gene of claim 4 has been transduced, and collecting the hyperthermostable protease from the culture.

\* \* \* \* \*

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
        ( A ) LENGTH: 903 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Met Asn Lys Lys Gly Leu Thr Val Leu Phe Ile Ala Ile Met Leu Leu
 1               5                  10                  15
Ser Val Val Pro Val His Phe Val Ser Ala Glu Thr Pro Pro Val Ser
            20                  25                  30
Ser Glu Asn Ser Thr Thr Ser Ile Leu Pro Asn Gln Gln Val Val Thr
        35                  40                  45
Lys Glu Val Ser Gln Ala Ala Leu Asn Ala Ile Met Lys Gly Gln Pro
 50                  55                  60
Asn Met Val Leu Ile Ile Lys Thr Lys Glu Gly Lys Leu Glu Glu Ala
 65                  70                  75                  80
Lys Thr Glu Leu Glu Lys Leu Gly Ala Glu Ile Leu Asp Glu Asn Arg
                85                  90                  95
Val Leu Asn Met Leu Leu Val Lys Ile Lys Pro Glu Lys Val Lys Glu
                100                 105                 110
Leu Asn Tyr Ile Ser Ser Leu Glu Lys Ala Trp Leu Asn Arg Glu Val
            115                 120                 125
Lys Leu Ser Pro Pro Ile Val Glu Lys Asp Val Lys Thr Lys Glu Pro
        130                 135                 140
Ser Leu Glu Pro Lys Met Tyr Asn Ser Thr Trp Val Ile Asn Ala Leu
145                 150                 155                 160
Gln Phe Ile Gln Glu Phe Gly Tyr Asp Gly Ser Gly Val Val Val Ala
                165                 170                 175
Val Leu Asp Thr Gly Val Asp Pro Asn His Pro Phe Leu Ser Ile Thr
            180                 185                 190
Pro Asp Gly Arg Arg Lys Ile Ile Glu Trp Lys Asp Phe Thr Asp Glu
        195                 200                 205
Gly Phe Val Asp Thr Ser Phe Ser Phe Ser Lys Val Val Asn Gly Thr
210                 215                 220
Leu Ile Ile Asn Thr Thr Phe Gln Val Ala Ser Gly Leu Thr Leu Asn
225                 230                 235                 240
Glu Ser Thr Gly Leu Met Glu Tyr Val Val Lys Thr Val Tyr Val Ser
                245                 250                 255
Asn Val Thr Ile Gly Asn Ile Thr Ser Ala Asn Gly Ile Tyr His Phe
            260                 265                 270
Gly Leu Leu Pro Glu Arg Tyr Phe Asp Leu Asn Phe Asp Gly Asp Gln
        275                 280                 285
Glu Asp Phe Tyr Pro Val Leu Leu Val Asn Ser Thr Gly Asn Gly Tyr
    290                 295                 300
Asp Ile Ala Tyr Val Asp Thr Asp Leu Asp Tyr Asp Phe Thr Asp Glu
305                 310                 315                 320
```

-continued

| | | | | | | | | | | | | | | |
|---|---|---|---|---|---|---|---|---|---|---|---|---|---|---|
|Val|Pro|Leu|Gly|Gln<br>325|Tyr|Asn|Val|Thr<br>330|Tyr|Asp|Val|Ala|Val<br>335|Phe|Ser|
|Tyr|Tyr|Tyr|Gly<br>340|Pro|Leu|Asn|Tyr<br>345|Val|Leu|Ala|Glu|Ile<br>350|Asp|Pro|Asn|
|Gly|Glu|Tyr<br>355|Ala|Val|Phe|Gly|Trp<br>360|Asp|Gly|His|Gly|His<br>365|Gly|Thr|His|
|Val|Ala<br>370|Gly|Thr|Val|Ala|Gly<br>375|Tyr|Asp|Ser|Asn|Asn<br>380|Asp|Ala|Trp|Asp|
|Trp<br>385|Leu|Ser|Met|Tyr|Ser<br>390|Gly|Glu|Trp|Glu|Val<br>395|Phe|Ser|Arg|Leu|Tyr<br>400|
|Gly|Trp|Asp|Tyr|Thr<br>405|Asn|Val|Thr|Thr|Asp<br>410|Thr|Val|Gln|Gly|Val<br>415|Ala|
|Pro|Gly|Ala|Gln<br>420|Ile|Met|Ala|Ile|Arg<br>425|Val|Leu|Arg|Ser|Asp<br>430|Gly|Arg|
|Gly|Ser|Met<br>435|Trp|Asp|Ile|Ile|Glu<br>440|Gly|Met|Thr|Tyr|Ala<br>445|Ala|Thr|His|
|Gly|Ala<br>450|Asp|Val|Ile|Ser|Met<br>455|Ser|Leu|Gly|Gly|Asn<br>460|Ala|Pro|Tyr|Leu|
|Asp<br>465|Gly|Thr|Asp|Pro|Glu<br>470|Ser|Val|Ala|Val|Asp<br>475|Glu|Leu|Thr|Glu|Lys<br>480|
|Tyr|Gly|Val|Val|Phe<br>485|Val|Ile|Ala|Ala|Gly<br>490|Asn|Glu|Gly|Pro|Gly<br>495|Ile|
|Asn|Ile|Val|Gly<br>500|Ser|Pro|Gly|Val|Ala<br>505|Thr|Lys|Ala|Ile|Thr<br>510|Val|Gly|
|Ala|Ala|Ala<br>515|Val|Pro|Ile|Asn|Val<br>520|Gly|Val|Tyr|Val|Ser<br>525|Gln|Ala|Leu|
|Gly|Tyr<br>530|Pro|Asp|Tyr|Tyr|Gly<br>535|Phe|Tyr|Tyr|Phe|Pro<br>540|Ala|Tyr|Thr|Asn|
|Val<br>545|Arg|Ile|Ala|Phe|Phe<br>550|Ser|Ser|Arg|Gly|Pro<br>555|Arg|Ile|Asp|Gly|Glu<br>560|
|Ile|Lys|Pro|Asn|Val<br>565|Val|Ala|Pro|Gly|Tyr<br>570|Gly|Ile|Tyr|Ser|Ser<br>575|Leu|
|Pro|Met|Trp|Ile<br>580|Gly|Gly|Ala|Asp|Phe<br>585|Met|Ser|Gly|Thr|Ser<br>590|Met|Ala|
|Thr|Pro|His<br>595|Val|Ser|Gly|Val|Val<br>600|Ala|Leu|Leu|Ile|Ser<br>605|Gly|Ala|Lys|
|Ala|Glu<br>610|Gly|Ile|Tyr|Tyr|Asn<br>615|Pro|Asp|Ile|Ile|Lys<br>620|Lys|Val|Leu|Glu|
|Ser<br>625|Gly|Ala|Thr|Trp|Leu<br>630|Glu|Gly|Asp|Pro|Tyr<br>635|Thr|Gly|Gln|Lys|Tyr<br>640|
|Thr|Glu|Leu|Asp|Gln<br>645|Gly|His|Gly|Leu|Val<br>650|Asn|Val|Thr|Lys|Ser<br>655|Trp|
|Glu|Ile|Leu|Lys<br>660|Ala|Ile|Asn|Gly|Thr<br>665|Thr|Leu|Pro|Ile|Val<br>670|Asp|His|
|Trp|Ala|Asp<br>675|Lys|Ser|Tyr|Ser|Asp<br>680|Phe|Ala|Glu|Tyr|Leu<br>685|Gly|Val|Asp|
|Val|Ile|Arg<br>690|Gly|Leu|Tyr|Ala|Arg<br>695|Asn|Ser|Ile|Pro|Asp<br>700|Ile|Val|Glu|
|Trp|His<br>705|Ile|Lys|Tyr|Val|Gly<br>710|Asp|Thr|Glu|Tyr|Arg<br>715|Thr|Phe|Glu|Ile<br>720|
|Tyr|Ala|Thr|Glu|Pro<br>725|Trp|Ile|Lys|Pro|Phe<br>730|Val|Ser|Gly|Ser|Val<br>735|Ile|
|Leu|Glu|Asn|Asn|Thr<br>740|Glu|Phe|Val|Leu|Arg<br>745|Val|Lys|Tyr|Asp|Val<br>750|Glu|

| | | | | | | | | | | | | | | |
|---|---|---|---|---|---|---|---|---|---|---|---|---|---|---|
| Gly | Leu | Glu<br>755 | Pro | Gly | Leu | Tyr | Val<br>760 | Gly | Arg | Ile | Ile<br>765 | Ile | Asp | Asp | Pro |
| Thr | Thr<br>770 | Pro | Val | Ile | Glu | Asp<br>775 | Glu | Ile | Leu | Asn | Thr<br>780 | Ile | Val | Ile | Pro |
| Glu<br>785 | Lys | Phe | Thr | Pro | Glu<br>790 | Asn | Asn | Tyr | Thr | Leu<br>795 | Thr | Trp | Tyr | Asp | Ile<br>800 |
| Asn | Gly | Pro | Glu | Met<br>805 | Val | Thr | His | His | Phe<br>810 | Phe | Thr | Val | Pro | Glu<br>815 | Gly |
| Val | Asp | Val | Leu<br>820 | Tyr | Ala | Met | Thr | Thr<br>825 | Tyr | Trp | Asp | Tyr | Gly<br>830 | Leu | Tyr |
| Arg | Pro | Asp<br>835 | Gly | Met | Phe | Val | Phe<br>840 | Pro | Tyr | Gln | Leu | Asp<br>845 | Tyr | Leu | Pro |
| Ala | Ala<br>850 | Val | Ser | Asn | Pro | Met<br>855 | Pro | Gly | Asn | Trp | Glu<br>860 | Leu | Val | Trp | Thr |
| Gly<br>865 | Phe | Asn | Phe | Ala | Pro<br>870 | Leu | Tyr | Glu | Ser | Gly<br>875 | Phe | Leu | Val | Arg | Ile<br>880 |
| Tyr | Gly | Val | Glu | Ile<br>885 | Thr | Pro | Ser | Val | Trp<br>890 | Tyr | Ile | Asn | Arg | Thr<br>895 | Tyr |
| Leu | Asp | Thr | Asn<br>900 | Thr | Glu | Phe | | | | | | | | | |

( 2 ) INFORMATION FOR SEQ ID NO:2:

( i ) SEQUENCE CHARACTERISTICS:
( A ) LENGTH: 2835 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:2:

```
TTTAAATTAT AAGATATAAT CACTCCGAGT GATGAGTAAG ATACATCATT ACAGTCCCAA      60
AATGTTTATA ATTGGAACGC AGTGAATATA CAAAATGAAT ATAACCTCGG AGGTGACTGT     120
AGAATGAATA AGAAGGGACT TACTGTGCTA TTTATAGCGA TAATGCTCCT TTCAGTAGTT     180
CCAGTGCACT TTGTGTCCGC AGAAACACCA CCGGTTAGTT CAGAAAATTC AACAACTTCT     240
ATACTCCCTA ACCAACAAGT TGTGACAAAA GAAGTTTCAC AAGCGGCGCT TAATGCTATA     300
ATGAAAGGAC AACCCAACAT GGTTCTTATA ATCAAGACTA AGGAAGGCAA ACTTGAAGAG     360
GCAAAAACCG AGCTTGAAAA GCTAGGTGCA GAGATTCTTG ACGAAAATAG AGTTCTTAAC     420
ATGTTGCTAG TTAAGATTAA GCCTGAGAAA GTTAAAGAGC TCAACTATAT CTCATCTCTT     480
GAAAAAGCCT GGCTTAACAG AGAAGTTAAG CTTTCCCCTC CAATTGTCGA AAAGGACGTC     540
AAGACTAAGG AGCCCTCCCT AGAACCAAAA ATGTATAACA GCACCTGGGT AATTAATGCT     600
CTCCAGTTCA TCCAGGAATT TGGATATGAT GGTAGTGGTG TTGTTGTTGC AGTACTTGAC     660
ACGGGAGTTG ATCCGAACCA TCCTTTCTTG AGCATAACTC CAGATGGACG CAGGAAAATT     720
ATAGAATGGA AGGATTTTAC AGACGAGGGA TTCGTGGATA CATCATTCAG CTTTAGCAAG     780
GTTGTAAATG GGACTCTTAT AATTAACACA ACATTCCAAG TGGCCTCAGG TCTCACGCTG     840
AATGAATCGA CAGGACTTAT GGAATACGTT GTTAAGACTG TTTACGTGAG CAATGTGACC     900
ATTGGAAATA TCACTTCTGC TAATGGCATC TATCACTTCG GCCTGCTCCC AGAAAGATAC     960
TTCGACTTAA ACTTCGATGG TGATCAAGAG GACTTCTATC CTGTCTTATT AGTTAACTCC    1020
ACTGGCAATG GTTATGACAT TGCATATGTG GATACTGACC TTGACTACGA CTTCACCGAC    1080
```

| | | | | | |
|---|---|---|---|---|---|
| GAAGTTCCAC | TTGGCCAGTA | CAACGTTACT | TATGATGTTG | CTGTTTTTAG | CTACTACTAC | 1140 |
| GGTCCTCTCA | ACTACGTGCT | TGCAGAAATA | GATCCTAACG | GAGAATATGC | AGTATTTGGG | 1200 |
| TGGGATGGTC | ACGGTCACGG | AACTCACGTA | GCTGGAACTG | TTGCTGGTTA | CGACAGCAAC | 1260 |
| AATGATGCTT | GGGATTGGCT | CAGTATGTAC | TCTGGTGAAT | GGAAGTGTT | CTCAAGACTC | 1320 |
| TATGGTTGGG | ATTATACGAA | CGTTACCACA | GACACCGTGC | AGGGTGTTGC | TCCAGGTGCC | 1380 |
| CAAATAATGG | CAATAAGAGT | TCTTAGGAGT | GATGGACGGG | GTAGCATGTG | GGATATTATA | 1440 |
| GAAGGTATGA | CATACGCAGC | AACCCATGGT | GCAGACGTTA | TAAGCATGAG | TCTCGGTGGA | 1500 |
| AATGCTCCAT | ACTTAGATGG | TACTGATCCA | GAAAGCGTTG | CTGTGGATGA | GCTTACCGAA | 1560 |
| AAGTACGGTG | TTGTATTCGT | AATAGCTGCA | GGAAATGAAG | GTCCTGGCAT | TAACATCGTT | 1620 |
| GGAAGTCCTG | GTGTTGCAAC | AAAGGCAATA | ACTGTTGGAG | CTGCTGCAGT | GCCCATTAAC | 1680 |
| GTTGGAGTTT | ATGTTTCCCA | AGCACTTGGA | TATCCTGATT | ACTATGGATT | CTATTACTTC | 1740 |
| CCCGCCTACA | CAAACGTTAG | AATAGCATTC | TTCTCAAGCA | GAGGGCCGAG | AATAGATGGT | 1800 |
| GAAATAAAAC | CCAATGTAGT | GGCTCCAGGT | TACGGAATTT | ACTCATCCCT | GCCGATGTGG | 1860 |
| ATTGGCGGAG | CTGACTTCAT | GTCTGGAACT | TCGATGGCTA | CTCCACATGT | CAGCGGTGTC | 1920 |
| GTTGCACTCC | TCATAAGCGG | GGCAAAGGCC | GAGGGAATAT | ACTACAATCC | AGATATAATT | 1980 |
| AAGAAGGTTC | TTGAGAGCGG | TGCAACCTGG | CTTGAGGGAG | ATCCATATAC | TGGGCAGAAG | 2040 |
| TACACTGAGC | TTGACCAAGG | TCATGGTCTT | GTTAACGTTA | CCAAGTCCTG | GAAATCCTT | 2100 |
| AAGGCTATAA | ACGGCACCAC | TCTCCCAATT | GTTGATCACT | GGGCAGACAA | GTCCTACAGC | 2160 |
| GACTTTGCGG | AGTACTTGGG | TGTGGACGTT | ATAAGAGGTC | TCTACGCAAG | GAACTCTATA | 2220 |
| CCTGACATTG | TCGAGTGGCA | CATTAAGTAC | GTAGGGGACA | CGGAGTACAG | AACTTTTGAG | 2280 |
| ATCTATGCAA | CTGAGCCATG | GATTAAGCCT | TTTGTCAGTG | GAAGTGTAAT | TCTAGAGAAC | 2340 |
| AATACCGAGT | TTGTCCTTAG | GGTGAAATAT | GATGTAGAGG | GTCTTGAGCC | AGGTCTCTAT | 2400 |
| GTTGGAAGGA | TAATCATTGA | TGATCCAACA | ACGCCAGTTA | TTGAAGACGA | GATCTTGAAC | 2460 |
| ACAATTGTTA | TTCCCGAGAA | GTTCACTCCT | GAGAACAATT | ACACCCTCAC | CTGGTATGAT | 2520 |
| ATTAATGGTC | CAGAAATGGT | GACTCACCAC | TTCTTCACTG | TGCCTGAGGG | AGTGGACGTT | 2580 |
| CTCTACGCGA | TGACCACATA | CTGGGACTAC | GGTCTGTACA | GACCAGATGG | AATGTTTGTG | 2640 |
| TTCCCATACC | AGCTAGATTA | TCTTCCCGCT | GCAGTCTCAA | ATCCAATGCC | TGGAAACTGG | 2700 |
| GAGCTAGTAT | GGACTGGATT | TAACTTTGCA | CCCCTCTATG | AGTCGGGCTT | CCTTGTAAGG | 2760 |
| ATTTACGGAG | TAGAGATAAC | TCCAAGCGTT | TGGTACATTA | ACAGGACATA | CCTTGACACT | 2820 |
| AACACTGAAT | TCTAG | | | | | 2835 |

( 2 ) INFORMATION FOR SEQ ID NO:3:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

GGWWSDRRTG TTRRHGTHGC DGTDMTYGAC ACSGG     35

( 2 ) INFORMATION FOR SEQ ID NO:4:

( i ) SEQUENCE CHARACTERISTICS:
        ( A ) LENGTH: 32 base pairs ( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:4:

KSTCACGGAA CTCACGTDGC BGGMACDGTT GC                    32

( 2 ) INFORMATION FOR SEQ ID NO:5:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:5:

ASCMGCAACH GTKCCVGCHA CGTGAGTTCC GTG                   33

( 2 ) INFORMATION FOR SEQ ID NO:6:

( i ) SEQUENCE CHARACTERISTICS:
( A ) LENGTH: 34 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:6:

CHCCGSYVAC RTGBGGAGWD GCCATBGAVG TDCC                  34

( 2 ) INFORMATION FOR SEQ ID NO:7:

( i ) SEQUENCE CHARACTERISTICS:
( A ) LENGTH: 898 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:7:

| | | | | | | |
|---|---|---|---|---|---|---|
| GATCTGAAGG | GCAAGGTCAT | AGGCTGGTAC | GACGCCGTCA | ACGGCAGGTC | GACCCCCTAC | 60 |
| GATGACCAGG | GACACGGAAC | CCACGTTGCG | GGTATCGTTG | CCGGAACCGG | CAGCGTTAAC | 120 |
| TCCCAGTACA | TAGGCGTCGC | CCCCGGCGCG | AAGCTCGTCG | GCGTCAAGGT | TCTCGGTGCC | 180 |
| GACGGTTCGG | GAAGCGTCTC | CACCATCATC | GCGGGTGTTG | ACTGGGTCGT | CCAGAACAAG | 240 |
| GACAAGTACG | GGATAAGGGT | CATCAACCTC | TCCCTCGGCT | CCTCCCAGAG | CTCCGACGGA | 300 |
| ACCGACTCCC | TCAGTCAGGC | CGTCAACAAC | GCCTGGGACG | CCGGTATAGT | AGTCTGCGTC | 360 |
| GCCGCCGGCA | ACAGCGGGCC | GAACACCTAC | ACCGTCGGCT | CACCCGCCGC | CGCGAGCAAG | 420 |
| GTCATAACCG | TCGGTGCAGT | TGACAGCAAC | GACAACATCG | CCAGCTTCTC | CAGCAGGGGA | 480 |
| CCGACCGCGG | ACGGAAGGCT | CAAGCCGGAA | GTCGTCGCCC | CCGGCGTTGA | CATCATAGCC | 540 |
| CCGCGCGCCA | GCGGAACCAG | CATGGGCACC | CCGATAAACG | ACTACTNCAA | CAAGGGCTCT | 600 |
| GGATCCAGCA | TGGACACCCC | GCACGTTTCG | GGCGTTGGCG | GCTCATCCT | CCAGGCCCAC | 660 |
| CCGAGCTGGA | CCCCGGACAA | GGTGAAGACG | CCCTCATCGA | GACCGCCGAC | ATAGTCGNCC | 720 |
| CCAAGGAGAT | AGCGGACATC | GCCTACGGTG | CGGGTAGGGT | GAACGTCTTC | AAGGGCATCA | 780 |
| AGTNCGACGA | CTACGNCAAG | NTCACCTTCA | CCGGNTCCGT | CGGCGACAAG | GGAAGGGGCA | 840 |

```
CCACACCTTC  GACGTCAGNG  GGGGCACTTC  GTGAACGNCA  CCCTCTNCTN  GGACANGG          898
```

( 2 ) INFORMATION FOR SEQ ID NO:8:

( i ) SEQUENCE CHARACTERISTICS:
        ( A ) LENGTH: 4765 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:8:

```
TTTAAATTAT  AAGATATAAT  CACTCCGAGT  GATGAGTAAG  ATACATCATT  ACAGTCCCAA          60
AATGTTTATA  ATTGGAACGC  AGTGAATATA  CAAAATGAAT  ATAACCTCGG  AGGTGACTGT         120
AGAATGAATA  AGAAGGGACT  TACTGTGCTA  TTTATAGCGA  TAATGCTCCT  TTCAGTAGTT         180
CCAGTGCACT  TTGTGTCCGC  AGAAACACCA  CCGGTTAGTT  CAGAAAATTC  AACAACTTCT         240
ATACTCCCTA  ACCAACAAGT  TGTGACAAAA  GAAGTTTCAC  AAGCGGCGCT  TAATGCTATA         300
ATGAAAGGAC  AACCCAACAT  GGTTCTTATA  ATCAAGACTA  AGGAAGGCAA  ACTTGAAGAG         360
GCAAAAACCG  AGCTTGAAAA  GCTAGGTGCA  GAGATTCTTG  ACGAAATAG   AGTTCTTAAC         420
ATGTTGCTAG  TTAAGATTAA  GCCTGAGAAA  GTTAAGAGC   TCAACTATAT  CTCATCTCTT         480
GAAAAAGCCT  GGCTTAACAG  AGAAGTTAAG  CTTTCCCCTC  CAATTGTCGA  AAAGGACGTC         540
AAGACTAAGG  AGCCCTCCCT  AGAACCAAAA  ATGTATAACA  GCACCTGGGT  AATTAATGCT         600
CTCCAGTTCA  TCCAGGAATT  TGGATATGAT  GGTAGTGGTG  TTGTTGTTGC  AGTACTTGAC         660
ACGGGAGTTG  ATCCGAACCA  TCCTTTCTTG  AGCATAACTC  CAGATGGACG  CAGGAAAATT         720
ATAGAATGGA  AGGATTTTAC  AGACGAGGGA  TTCGTGGATA  CATCATTCAG  CTTTAGCAAG         780
GTTGTAAATG  GGACTCTTAT  AATTAACACA  ACATTCCAAG  TGGCCTCAGG  TCTCACGCTG         840
AATGAATCGA  CAGGACTTAT  GGAATACGTT  GTTAAGACTG  TTTACGTGAG  CAATGTGACC         900
ATTGGAAATA  TCACTTCTGC  TAATGGCATC  TATCACTTCG  GCCTGCTCCC  AGAAAGATAC         960
TTCGACTTAA  ACTTCGATGG  TGATCAAGAG  GACTTCTATC  CTGTCTTATT  AGTTAACTCC        1020
ACTGGCAATG  GTTATGACAT  TGCATATGTG  GATACTGACC  TTGACTACGA  CTTCACCGAC        1080
GAAGTTCCAC  TTGGCCAGTA  CAACGTTACT  TATGATGTTG  CTGTTTTTAG  CTACTACTAC        1140
GGTCCTCTCA  ACTACGTGCT  TGCAGAAATA  GATCCTAACG  GAGAATATGC  AGTATTTGGG        1200
TGGGATGGTC  ACGGTCACGG  AACTCACGTA  GCTGGAACTG  TTGCTGGTTA  CGACAGCAAC        1260
AATGATGCTT  GGGATTGGCT  CAGTATGTAC  TCTGGTGAAT  GGGAAGTGTT  CTCAAGACTC        1320
TATGGTTGGG  ATTATACGAA  CGTTACCACA  GACACCGTGC  AGGGTGTTGC  TCCAGGTGCC        1380
CAAATAATGG  CAATAAGAGT  TCTTAGGAGT  GATGGACGGG  GTAGCATGTG  GGATATTATA        1440
GAAGGTATGA  CATACGCAGC  AACCCATGGT  GCAGACGTTA  TAAGCATGAG  TCTCGGTGGA        1500
AATGCTCCAT  ACTTAGATGG  TACTGATCCA  GAAAGCGTTG  CTGTGGATGA  GCTTACCGAA        1560
AAGTACGGTG  TTGTATTCGT  AATAGCTGCA  GGAAATGAAG  GTCCTGGCAT  TAACATCGTT        1620
GGAAGTCCTG  GTGTTGCAAC  AAAGGCAATA  ACTGTTGGAG  CTGCTGCAGT  GCCCATTAAC        1680
GTTGGAGTTT  ATGTTTCCCA  AGCACTTGGA  TATCCTGATT  ACTATGGATT  CTATTACTTC        1740
CCCGCCTACA  CAAACGTTAG  AATAGCATTC  TTCTCAAGCA  GAGGGCCGAG  AATAGATGGT        1800
GAAATAAAAC  CCAATGTAGT  GGCTCCAGGT  TACGGAATTT  ACTCATCCCT  GCCGATGTGG        1860
ATTGGCGGAG  CTGACTTCAT  GTCTGGAACT  TCGATGGCTA  CTCCACATGT  CAGCGGTGTC        1920
```

```
GTTGCACTCC TCATAAGCGG GGCAAAGGCC GAGGGAATAT ACTACAATCC AGATATAATT      1980
AAGAAGGTTC TTGAGAGCGG TGCAACCTGG CTTGAGGGAG ATCCATATAC TGGGCAGAAG      2040
TACACTGAGC TTGACCAAGG TCATGGTCTT GTTAACGTTA CCAAGTCCTG GGAAATCCTT      2100
AAGGCTATAA ACGGCACCAC TCTCCCAATT GTTGATCACT GGGCAGACAA GTCCTACAGC      2160
GACTTTGCGG AGTACTTGGG TGTGGACGTT ATAAGAGGTC TCTACGCAAG GAACTCTATA      2220
CCTGACATTG TCGAGTGGCA CATTAAGTAC GTAGGGGACA CGGAGTACAG AACTTTTGAG      2280
ATCTATGCAA CTGAGCCATG GATTAAGCCT TTTGTCAGTG GAAGTGTAAT TCTAGAGAAC      2340
AATACCGAGT TTGTCCTTAG GGTGAAATAT GATGTAGAGG GTCTTGAGCC AGGTCTCTAT      2400
GTTGGAAGGA TAATCATTGA TGATCCAACA ACGCCAGTTA TTGAAGACGA GATCTTGAAC      2460
ACAATTGTTA TTCCCGAGAA GTTCACTCCT GAGAACAATT ACACCCTCAC CTGGTATGAT      2520
ATTAATGGTC CAGAAATGGT GACTCACCAC TTCTTCACTG TGCCTGAGGG AGTGGACGTT      2580
CTCTACGCGA TGACCACATA CTGGGACTAC GGTCTGTACA GACCAGATGG AATGTTTGTG      2640
TTCCCATACC AGCTAGATTA TCTTCCCGCT GCAGTCTCAA ATCCAATGCC TGGAAACTGG      2700
GAGCTAGTAT GGACTGGATT TAACTTTGCA CCCCTCTATG AGTCGGGCTT CCTTGTAAGG      2760
ATTTACGGAG TAGAGATAAC TCCAAGCGTT TGGTACATTA ACAGGACATA CCTTGACACT      2820
AACACTGAAT TCTCAATTGA ATTCAATATT ACTAACATCT ATGCCCCAAT TAATGCAACT      2880
CTAATCCCCA TTGGCCTTGG AACCTACAAT GCGAGCGTTG AAAGCGTTGG TGATGGAGAG      2940
TTCTTCATAA AGGGCATTGA AGTTCCTGAA GGCACCGCAG AGTTGAAGAT TAGGATAGGC      3000
AACCCAAGTG TTCCGAATTC AGATCTAGAC TTGTACCTTT ATGACAGTAA AGGCAATTTA      3060
GTGGCCTTAG ATGGAAACCC AACAGCAGAA GAAGAGGTTG TAGTTGAGTA TCCTAAGCCT      3120
GGAGTTTATT CAATAGTAGT ACATGGTTAC AGCGTCAGGG ACGAAAATGG TAATCCAACG      3180
ACAACCACCT TTGACTTAGT TGTTCAAATG ACCCTTGATA ATGGAAACAT AAAGCTTGAC      3240
AAAGACTCGA TTATTCTTGG AAGCAATGAA AGCGTAGTTG TAACTGCAAA CATAACAATT      3300
GATAGAGATC ATCCTACAGG AGTATACTCT GGTATCATAG AGATTAGAGA TAATGAGGTC      3360
TACCAGGATA CAAATACTTC AATTGCGAAA ATACCCATAA CTTTGGTAAT TGACAAGGCG      3420
GACTTTGCCG TTGGTCTCAC ACCAGCAGAG GGAGTACTTG GAGAGGCTAG AAATTACACT      3480
CTAATTGTAA AGCATGCCCT AACACTAGAG CCTGTGCCAA ATGCTACAGT GATTATAGGA      3540
AACTACACCT ACCTCACAGA CGAAAACGGT ACAGTGACAT TCACGTATGC TCCAACTAAG      3600
TTAGGCAGTG ATGAAATCAC AGTCATAGTT AAGAAAGAGA ACTTCAACAC ATTAGAGAAG      3660
ACCTTCCAAA TCACAGTATC AGAGCCTGAA ATAACTGAAG AGGACATAAA TGAGCCCAAG      3720
CTTGCAATGT CATCACCAGA AGCAAATGCT ACCATAGTAT CAGTTGAGAT GGAGAGTGAG      3780
GGTGGCGTTA AAAAGACAGT GACAGTGGAA ATAACTATAA ACGGAACCGC TAATGAGACT      3840
GCAACAATAG TGGTTCCTGT TCCTAAGAAG GCCGAAAACA TCGAGGTAAG TGGAGACCAC      3900
GTAATTTCCT ATAGTATAGA GGAAGGAGAG TACGCCAAGT ACGTTATAAT TACAGTGAAG      3960
TTTGCATCAC CTGTAACAGT AACTGTTACT TACACTATCT ATGCTGGCCC AAGAGTCTCA      4020
ATCTTGACAC TTAACTTCCT TGGCTACTCA TGGTACAGAC TATATTCACA GAAGTTTGAC      4080
GAATTGTACC AAAAGGCCCT TGAATTGGGA GTGGACAACG AGACATTAGC TTTAGCCCTC      4140
AGCTACCATG AAAAAGCCAA AGAGTACTAC GAAAAGGCCC TTGAGCTTAG CGAGGGTAAC      4200
ATAATCCAAT ACCTTGGAGA CATAAGACTA TTACCTCCAT TAAGACAGGC ATACATCAAT      4260
GAAATGAAGG CAGTTAAGAT ACTGGAAAAG GCCATAGAAG AATTAGAGGG TGAAGAGTAA      4320
```

-continued

```
TCTCCAATTT TTCCCACTTT TTCTTTTATA ACATTCCAAG CCTTTTCTTA GCTTCTTCGC     4380
TCATTCTATC AGGAGTCCAT GGAGGATCAA AGGTAAGTTC AACCTCCACA TCTCTTACTC     4440
CTGGGATTTC GAGTACTTTC TCCTCTACAG CTCTAAGAAG CCAGAGAGTT AAAGGACACC     4500
CAGGAGTTGT CATTGTCATC TTTATATATA CCGTTTTGTC AGGATTAATC TTTAGCTCAT     4560
AAATTAATCC AAGGTTTACA ACATCCATCC CAATTCTGG GTCGATAACC TCCTTTAGCT      4620
TTTCCAGAAT CATTTCTTCA GTAATTTCAA GGTTCTCATC TTTGGTTTCT CTCACAAACC     4680
CAATTTCAAC CTGCCTGATA CCTTCTAACT CCCTAAGCTT GTTATATATC TCCAAAAGAG     4740
TGGCATCATC AATTTTCTCT TTAAA                                           4765
```

( 2 ) INFORMATION FOR SEQ ID NO:9:

( i ) SEQUENCE CHARACTERISTICS:
        ( A ) LENGTH: 1398 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:9:

```
Met Asn Lys Lys Gly Leu Thr Val Leu Phe Ile Ala Ile Met Leu Leu
  1               5                  10                  15

Ser Val Val Pro Val His Phe Val Ser Ala Glu Thr Pro Pro Val Ser
                 20                  25                  30

Ser Glu Asn Ser Thr Thr Ser Ile Leu Pro Asn Gln Gln Val Val Thr
             35                  40                  45

Lys Glu Val Ser Gln Ala Ala Leu Asn Ala Ile Met Lys Gly Gln Pro
         50                  55                  60

Asn Met Val Leu Ile Ile Lys Thr Lys Glu Gly Lys Leu Glu Glu Ala
 65                  70                  75                  80

Lys Thr Glu Leu Glu Lys Leu Gly Ala Glu Ile Leu Asp Glu Asn Arg
                 85                  90                  95

Val Leu Asn Met Leu Leu Val Lys Ile Lys Pro Glu Lys Val Lys Glu
                100                 105                 110

Leu Asn Tyr Ile Ser Ser Leu Lys Ala Trp Leu Asn Arg Glu Val
            115                 120                 125

Lys Leu Ser Pro Pro Ile Val Glu Lys Asp Val Lys Thr Lys Glu Pro
        130                 135                 140

Ser Leu Glu Pro Lys Met Tyr Asn Ser Thr Trp Val Ile Asn Ala Leu
145                 150                 155                 160

Gln Phe Ile Gln Glu Phe Gly Tyr Asp Gly Ser Gly Val Val Val Ala
                165                 170                 175

Val Leu Asp Thr Gly Val Asp Pro Asn His Pro Phe Leu Ser Ile Thr
            180                 185                 190

Pro Asp Gly Arg Arg Lys Ile Ile Glu Trp Lys Asp Phe Thr Asp Glu
        195                 200                 205

Gly Phe Val Asp Thr Ser Phe Ser Phe Ser Lys Val Val Asn Gly Thr
    210                 215                 220

Leu Ile Ile Asn Thr Thr Phe Gln Val Ala Ser Gly Leu Thr Leu Asn
225                 230                 235                 240

Glu Ser Thr Gly Leu Met Glu Tyr Val Val Lys Thr Val Tyr Val Ser
                245                 250                 255

Asn Val Thr Ile Gly Asn Ile Thr Ser Ala Asn Gly Ile Tyr His Phe
            260                 265                 270
```

-continued

| | | | | | | | | | | | | | | |
|---|---|---|---|---|---|---|---|---|---|---|---|---|---|---|
|Gly|Leu|Leu 275|Pro|Glu|Arg|Tyr|Phe 280|Asp|Leu|Asn|Phe|Gly 285|Asp|Gln|
|Glu|Asp 290|Phe|Tyr|Pro|Val|Leu 295|Leu|Val|Asn|Ser|Thr 300|Gly|Asn|Gly|Tyr|
|Asp 305|Ile|Ala|Tyr|Val|Asp 310|Thr|Asp|Leu|Asp|Tyr 315|Asp|Phe|Thr|Asp|Glu 320|
|Val|Pro|Leu|Gly|Gln 325|Tyr|Asn|Val|Thr 330|Tyr|Asp|Val|Ala|Val|Phe 335|Ser|
|Tyr|Tyr|Tyr|Gly 340|Pro|Leu|Asn|Tyr|Val 345|Leu|Ala|Glu|Ile|Asp 350|Pro|Asn|
|Gly|Glu|Tyr 355|Ala|Val|Phe|Gly|Trp 360|Asp|Gly|His|Gly|His 365|Gly|Thr|His|
|Val|Ala 370|Gly|Thr|Val|Ala|Gly 375|Tyr|Asp|Ser|Asn|Asn 380|Asp|Ala|Trp|Asp|
|Trp 385|Leu|Ser|Met|Tyr|Ser 390|Gly|Glu|Trp|Glu|Val 395|Phe|Ser|Arg|Leu|Tyr 400|
|Gly|Trp|Asp|Tyr|Thr 405|Asn|Val|Thr|Thr 410|Asp|Thr|Val|Gln|Gly|Val 415|Ala|
|Pro|Gly|Ala|Gln 420|Ile|Met|Ala|Ile|Arg 425|Val|Leu|Arg|Ser|Asp 430|Gly|Arg|
|Gly|Ser|Met 435|Trp|Asp|Ile|Ile|Glu 440|Gly|Met|Thr|Tyr|Ala 445|Ala|Thr|His|
|Gly|Ala|Asp 450|Val|Ile|Ser|Met 455|Ser|Leu|Gly|Gly|Asn 460|Ala|Pro|Tyr|Leu|
|Asp 465|Gly|Thr|Asp|Pro|Glu 470|Ser|Val|Ala|Val|Asp 475|Glu|Leu|Thr|Glu|Lys 480|
|Tyr|Gly|Val|Val|Phe 485|Val|Ile|Ala|Ala|Gly 490|Asn|Glu|Gly|Pro|Gly 495|Ile|
|Asn|Ile|Val|Gly 500|Ser|Pro|Gly|Val|Ala 505|Thr|Lys|Ala|Ile|Thr 510|Val|Gly|
|Ala|Ala|Ala 515|Val|Pro|Ile|Asn|Val 520|Gly|Val|Tyr|Val|Ser 525|Gln|Ala|Leu|
|Gly|Tyr 530|Pro|Asp|Tyr|Tyr|Gly 535|Phe|Tyr|Tyr|Phe|Pro 540|Ala|Tyr|Thr|Asn|
|Val 545|Arg|Ile|Ala|Phe|Phe 550|Ser|Ser|Arg|Gly|Pro 555|Arg|Ile|Asp|Gly|Glu 560|
|Ile|Lys|Pro|Asn|Val 565|Val|Ala|Pro|Gly|Tyr 570|Gly|Ile|Tyr|Ser|Ser 575|Leu|
|Pro|Met|Trp|Ile 580|Gly|Gly|Ala|Asp|Phe 585|Met|Ser|Gly|Thr|Ser 590|Met|Ala|
|Thr|Pro|His 595|Val|Ser|Gly|Val|Val 600|Ala|Leu|Leu|Ile|Ser 605|Gly|Ala|Lys|
|Ala|Glu 610|Gly|Ile|Tyr|Tyr|Asn 615|Pro|Asp|Ile|Ile|Lys 620|Lys|Val|Leu|Glu|
|Ser 625|Gly|Ala|Thr|Trp|Leu 630|Glu|Gly|Asp|Pro|Tyr 635|Thr|Gly|Gln|Lys|Tyr 640|
|Thr|Glu|Leu|Asp|Gln 645|Gly|His|Gly|Leu|Val 650|Asn|Val|Thr|Lys|Ser 655|Trp|
|Glu|Ile|Leu|Lys|Ala 660|Ile|Asn|Gly|Thr|Thr 665|Leu|Pro|Ile|Val|Asp 670|His|
|Trp|Ala|Asp|Lys 675|Ser|Tyr|Ser|Asp|Phe 680|Ala|Glu|Tyr|Leu 685|Gly|Val|Asp|
|Val|Ile|Arg 690|Gly|Leu|Tyr|Ala|Arg 695|Asn|Ser|Ile|Pro|Asp 700|Ile|Val|Glu|

-continued

```
Trp His Ile Lys Tyr Val Gly Asp Thr Glu Tyr Arg Thr Phe Glu Ile
705             710             715             720
Tyr Ala Thr Glu Pro Trp Ile Lys Pro Phe Val Ser Gly Ser Val Ile
            725             730             735
Leu Glu Asn Asn Thr Glu Phe Val Leu Arg Val Lys Tyr Asp Val Glu
            740             745             750
Gly Leu Glu Pro Gly Leu Tyr Val Gly Arg Ile Ile Ile Asp Asp Pro
            755             760             765
Thr Thr Pro Val Ile Glu Asp Glu Ile Leu Asn Thr Ile Val Ile Pro
770             775             780
Glu Lys Phe Thr Pro Glu Asn Asn Tyr Thr Leu Thr Trp Tyr Asp Ile
785             790             795             800
Asn Gly Pro Glu Met Val Thr His His Phe Phe Thr Val Pro Glu Gly
                805             810             815
Val Asp Val Leu Tyr Ala Met Thr Thr Tyr Trp Asp Tyr Gly Leu Tyr
            820             825             830
Arg Pro Asp Gly Met Phe Val Phe Pro Tyr Gln Leu Asp Tyr Leu Pro
            835             840             845
Ala Ala Val Ser Asn Pro Met Pro Gly Asn Trp Glu Leu Val Trp Thr
850             855             860
Gly Phe Asn Phe Ala Pro Leu Tyr Glu Ser Gly Phe Leu Val Arg Ile
865             870             875             880
Tyr Gly Val Glu Ile Thr Pro Ser Val Trp Tyr Ile Asn Arg Thr Tyr
                885             890             895
Leu Asp Thr Asn Thr Glu Phe Ser Ile Glu Phe Asn Ile Thr Asn Ile
            900             905             910
Tyr Ala Pro Ile Asn Ala Thr Leu Ile Pro Ile Gly Leu Gly Thr Tyr
            915             920             925
Asn Ala Ser Val Glu Ser Val Gly Asp Gly Glu Phe Phe Ile Lys Gly
930             935             940
Ile Glu Val Pro Glu Gly Thr Ala Glu Leu Lys Ile Arg Ile Gly Asn
945             950             955             960
Pro Ser Val Pro Asn Ser Asp Leu Asp Leu Tyr Leu Tyr Asp Ser Lys
            965             970             975
Gly Asn Leu Val Ala Leu Asp Gly Asn Pro Thr Ala Glu Glu Glu Val
            980             985             990
Val Val Glu Tyr Pro Lys Pro Gly Val Tyr Ser Ile Val Val His Gly
            995             1000            1005
Tyr Ser Val Arg Asp Glu Asn Gly Asn Pro Thr Thr Thr Phe Asp
1010            1015            1020
Leu Val Val Gln Met Thr Leu Asp Asn Gly Asn Ile Lys Leu Asp Lys
1025            1030            1035            1040
Asp Ser Ile Ile Leu Gly Ser Asn Glu Ser Val Val Val Thr Ala Asn
            1045            1050            1055
Ile Thr Ile Asp Arg Asp His Pro Thr Gly Val Tyr Ser Gly Ile Ile
            1060            1065            1070
Glu Ile Arg Asp Asn Glu Val Tyr Gln Asp Thr Asn Thr Ser Ile Ala
            1075            1080            1085
Lys Ile Pro Ile Thr Leu Val Ile Asp Lys Ala Asp Phe Ala Val Gly
            1090            1095            1100
Leu Thr Pro Ala Glu Gly Val Leu Gly Glu Ala Arg Asn Tyr Thr Leu
1105            1110            1115            1120
Ile Val Lys His Ala Leu Thr Leu Glu Pro Val Pro Asn Ala Thr Val
```

```
                                    1125                              1130                              1135
         Ile  Ile  Gly  Asn  Tyr  Thr  Tyr  Leu  Thr  Asp  Glu  Asn  Gly  Thr  Val  Thr
                        1140                              1145                        1150

Phe  Thr  Tyr  Ala  Pro  Thr  Lys  Leu  Gly  Ser  Asp  Glu  Ile  Thr  Val  Ile
                        1155                              1160                        1165

Val  Lys  Lys  Glu  Asn  Phe  Asn  Thr  Leu  Glu  Lys  Thr  Phe  Gln  Ile  Thr
                   1170                              1175                        1180

Val  Ser  Glu  Pro  Glu  Ile  Thr  Glu  Glu  Asp  Ile  Asn  Glu  Pro  Lys  Leu
         1185                         1190                              1195                   1200

Ala  Met  Ser  Ser  Pro  Glu  Ala  Asn  Ala  Thr  Ile  Val  Ser  Val  Glu  Met
                             1205                              1210                   1215

Glu  Ser  Glu  Gly  Gly  Val  Lys  Lys  Thr  Val  Thr  Val  Glu  Ile  Thr  Ile
                        1220                              1225                        1230

Asn  Gly  Thr  Ala  Asn  Glu  Thr  Ala  Thr  Ile  Val  Val  Pro  Val  Pro  Lys
                        1235                              1240                        1245

Lys  Ala  Glu  Asn  Ile  Glu  Val  Ser  Gly  Asp  His  Val  Ile  Ser  Tyr  Ser
                        1250                              1255                        1260

Ile  Glu  Glu  Gly  Glu  Tyr  Ala  Lys  Tyr  Val  Ile  Ile  Thr  Val  Lys  Phe
         1265                         1270                              1275                   1280

Ala  Ser  Pro  Val  Thr  Val  Thr  Val  Thr  Tyr  Thr  Ile  Tyr  Ala  Gly  Pro
                             1285                              1290                   1295

Arg  Val  Ser  Ile  Leu  Thr  Leu  Asn  Phe  Leu  Gly  Tyr  Ser  Trp  Tyr  Arg
                        1300                              1305                        1310

Leu  Tyr  Ser  Gln  Lys  Phe  Asp  Glu  Leu  Tyr  Gln  Lys  Ala  Leu  Glu  Leu
                        1315                              1320                        1325

Gly  Val  Asp  Asn  Glu  Thr  Leu  Ala  Leu  Ala  Leu  Ser  Tyr  His  Glu  Lys
                        1330                              1335                        1340

Ala  Lys  Glu  Tyr  Tyr  Glu  Lys  Ala  Leu  Glu  Leu  Ser  Glu  Gly  Asn  Ile
         1345                         1350                              1355                   1360

Ile  Gln  Tyr  Leu  Gly  Asp  Ile  Arg  Leu  Leu  Pro  Pro  Leu  Arg  Gln  Ala
                             1365                              1370                   1375

Tyr  Ile  Asn  Glu  Met  Lys  Ala  Val  Lys  Ile  Leu  Glu  Lys  Ala  Ile  Glu
                        1380                              1385                        1390

Glu  Leu  Glu  Gly  Glu  Glu
                        1395
```

( 2 ) INFORMATION FOR SEQ ID NO:10:

( i ) SEQUENCE CHARACTERISTICS:
        ( A ) LENGTH: 145 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 2..145

( x i ) SEQUENCE DESCRIPTION: SEQ ID NO:10:

```
A  GTT  GCG  GTA  ATT  GAC  ACG  GGT  ATA  GAC  GCG  AAC  CAC  CCC  GAT  CTG              46
   Val  Ala  Val  Ile  Asp  Thr  Gly  Ile  Asp  Ala  Asn  His  Pro  Asp  Leu
   1              5                        10                       15

AAG  GGC  AAG  GTC  ATA  GGC  TGG  TAC  GAC  GCC  GTC  AAC  GGC  AGG  TCG  ACC           94
Lys  Gly  Lys  Val  Ile  Gly  Trp  Tyr  Asp  Ala  Val  Asn  Gly  Arg  Ser  Thr
                    20                       25                       30

CCC  TAC  GAT  GAC  CAG  GGA  CAC  GGA  ACT  CAC  GTN  GCN  GGA  ACN  GTT  GCT          142
Pro  Tyr  Asp  Asp  Gln  Gly  His  Gly  Thr  His  Val  Ala  Gly  Thr  Val  Ala
```

```
                          35                    40                       45
GGT                                                                                          145
Gly ( 2 ) INFORMATION FOR SEQ ID NO:11:

( i ) SEQUENCE CHARACTERISTICS:
        ( A ) LENGTH: 564 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..564

( x i ) SEQUENCE DESCRIPTION: SEQ ID NO:11:

TCT  CAC  GGA  ACT  CAC  GTG  GCG  GGA  ACA  GTT  GCC  GGA  ACA  GGC  AGC  GTT     48
Ser  His  Gly  Thr  His  Val  Ala  Gly  Thr  Val  Ala  Gly  Thr  Gly  Ser  Val
     50                       55                       60

AAC  TCC  CAG  TAC  ATA  GGC  GTC  GCC  CCC  GGC  GCG  AAG  CTC  GTC  GGT  GTC     96
Asn  Ser  Gln  Tyr  Ile  Gly  Val  Ala  Pro  Gly  Ala  Lys  Leu  Val  Gly  Val
65                       70                       75                       80

AAG  GTT  CTC  GGT  GCC  GAC  GGT  TCG  GGA  AGC  GTC  TCC  ACC  ATC  ATC  GCG    144
Lys  Val  Leu  Gly  Ala  Asp  Gly  Ser  Gly  Ser  Val  Ser  Thr  Ile  Ile  Ala
                    85                       90                       95

GGT  GTT  GAC  TGG  GTC  GTC  CAG  AAC  AAG  GAT  AAG  TAC  GGG  ATA  AGG  GTC    192
Gly  Val  Asp  Trp  Val  Val  Gln  Asn  Lys  Asp  Lys  Tyr  Gly  Ile  Arg  Val
                    100                      105                      110

ATC  AAC  CTC  TCC  CTC  GGC  TCC  TCC  CAG  AGC  TCC  GAC  GGA  GCC  GAC  TCC    240
Ile  Asn  Leu  Ser  Leu  Gly  Ser  Ser  Gln  Ser  Ser  Asp  Gly  Ala  Asp  Ser
               115                      120                      125

CTC  AGT  CAG  GCC  GTC  AAC  AAC  GCC  TGG  GAC  GCC  GGT  ATA  GTA  GTC  TGC    288
Leu  Ser  Gln  Ala  Val  Asn  Asn  Ala  Trp  Asp  Ala  Gly  Ile  Val  Val  Cys
     130                      135                      140

GTC  GCC  GCC  GGC  AAC  AGC  GGG  CCG  AAC  ACC  TAC  ACC  GTC  GGC  TCA  CCC    336
Val  Ala  Ala  Gly  Asn  Ser  Gly  Pro  Asn  Thr  Tyr  Thr  Val  Gly  Ser  Pro
145                      150                      155                      160

GCC  GCC  GCG  AGC  AAG  GTC  ATA  ACC  GTC  GGT  GCA  GTT  GAC  AGC  AAC  GAC    384
Ala  Ala  Ala  Ser  Lys  Val  Ile  Thr  Val  Gly  Ala  Val  Asp  Ser  Asn  Asp
                    165                      170                      175

AAC  ATC  GCC  AGC  TTC  TCC  AGC  AGG  GGA  CCG  ACC  GCG  GAC  GGA  AGG  CTC    432
Asn  Ile  Ala  Ser  Phe  Ser  Ser  Arg  Gly  Pro  Thr  Ala  Asp  Gly  Arg  Leu
               180                      185                      190

AAG  CCG  GAA  GTC  GTC  GCC  CCC  GGC  GTT  GAC  ATC  ATA  GCC  CCG  CGC  GCC    480
Lys  Pro  Glu  Val  Val  Ala  Pro  Gly  Val  Asp  Ile  Ile  Ala  Pro  Arg  Ala
          195                      200                      205

AGC  GGA  ACC  AGC  ATG  GGC  ACC  CCG  ATA  AAC  GAC  TAC  TAC  ACC  AAG  GCC    528
Ser  Gly  Thr  Ser  Met  Gly  Thr  Pro  Ile  Asn  Asp  Tyr  Tyr  Thr  Lys  Ala
     210                      215                      220

TCT  GGA  ACC  TCA  ATG  GCC  ACT  CCC  CAT  GTT  ACC  GGT                         564
Ser  Gly  Thr  Ser  Met  Ala  Thr  Pro  His  Val  Thr  Gly
225                      230                      235

( 2 ) INFORMATION FOR SEQ ID NO:12:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA
```

( x i ) SEQUENCE DESCRIPTION: SEQ ID NO:12:

GGCAAGGTCA TAGGCTGGTA 20

( 2 ) INFORMATION FOR SEQ ID NO:13:

( i ) SEQUENCE CHARACTERISTICS:
　　　　　　　　( A ) LENGTH: 20 base pairs
　　　　　　　　( B ) TYPE: nucleic acid
　　　　　　　　( C ) STRANDEDNESS: single
　　　　　　　　( D ) TOPOLOGY: linear ( i i ) MOLECULE TYPE: cDNA ( x i ) SEQUENCE DESCRIPTION: SEQ ID NO:13:

CCAGAACAAG GATAAGTACG 20

( 2 ) INFORMATION FOR SEQ ID NO:14:

( i ) SEQUENCE CHARACTERISTICS:
　　　　　　　　( A ) LENGTH: 20 base pairs
　　　　　　　　( B ) TYPE: nucleic acid
　　　　　　　　( C ) STRANDEDNESS: single
　　　　　　　　( D ) TOPOLOGY: linear ( i i ) MOLECULE TYPE: cDNA ( x i ) SEQUENCE DESCRIPTION: SEQ ID NO:14:

GGCACCCCGA TAAACGACTA 20

( 2 ) INFORMATION FOR SEQ ID NO:15:

( i ) SEQUENCE CHARACTERISTICS:
　　　　　　　　( A ) LENGTH: 20 base pairs
　　　　　　　　( B ) TYPE: nucleic acid
　　　　　　　　( C ) STRANDEDNESS: single
　　　　　　　　( D ) TOPOLOGY: linear ( i i ) MOLECULE TYPE: cDNA ( x i ) SEQUENCE DESCRIPTION: SEQ ID NO:15:

ACGCCTATGT ACTGGGAGTT 20

( 2 ) INFORMATION FOR SEQ ID NO:16:

( i ) SEQUENCE CHARACTERISTICS:
　　　　　　　　( A ) LENGTH: 20 base pairs
　　　　　　　　( B ) TYPE: nucleic acid
　　　　　　　　( C ) STRANDEDNESS: single
　　　　　　　　( D ) TOPOLOGY: linear ( i i ) MOLECULE TYPE: cDNA ( x i ) SEQUENCE DESCRIPTION: SEQ ID NO:16:

CGTACTTATC CTTGTTCTGG 20

( 2 ) INFORMATION FOR SEQ ID NO:17:

( i ) SEQUENCE CHARACTERISTICS:
　　　　　　　　( A ) LENGTH: 20 base pairs
　　　　　　　　( B ) TYPE: nucleic acid
　　　　　　　　( C ) STRANDEDNESS: single
　　　　　　　　( D ) TOPOLOGY: linear ( i i ) MOLECULE TYPE: cDNA ( x i ) SEQUENCE DESCRIPTION: SEQ ID NO:17:

TGTAGTAGTC GTTTATCGGG 20

(2) INFORMATION FOR SEQ ID NO:18:

(i) SEQUENCE CHARACTERISTICS:
        (A) LENGTH: 237 amino acids
        (B) TYPE: amino acid
        (C) STRANDEDNESS: single
        (D) TOPOLOGY: linear (ii) MOLECULE TYPE: cDNA (xi) SEQUENCE DESCRIPTION: SEQ ID NO:18:

```
Asp Leu Lys Gly Lys Val Ile Gly Trp Tyr Asp Ala Val Asn Gly Arg
 1               5                  10                 15
Ser Thr Pro Tyr Asp Asp Gln Gly His Gly Thr His Val Ala Gly Ile
             20                  25                 30
Val Ala Gly Thr Gly Ser Val Asn Ser Gln Tyr Ile Gly Val Ala Pro
         35                  40                 45
Gly Ala Lys Leu Val Gly Val Lys Val Leu Gly Ala Asp Gly Ser Gly
     50                  55                 60
Ser Val Ser Thr Ile Ile Ala Gly Val Asp Trp Val Val Gln Asn Lys
 65                  70                 75                 80
Asp Xaa Tyr Gly Ile Arg Val Ile Asn Leu Ser Leu Gly Ser Ser Gln
                 85                  90                 95
Ser Ser Asp Gly Thr Asp Ser Leu Ser Gln Ala Val Asn Asn Ala Trp
            100                 105                110
Asp Ala Gly Ile Val Val Cys Val Ala Ala Gly Asn Ser Gly Pro Asn
            115                 120                125
Thr Tyr Thr Val Gly Ser Pro Ala Ala Ala Ser Lys Val Ile Thr Val
    130                 135                 140
Gly Ala Val Asp Ser Asn Asp Asn Ile Ala Ser Phe Ser Ser Arg Gly
145                 150                 155                160
Pro Thr Ala Asp Gly Arg Leu Lys Pro Glu Val Val Ala Pro Gly Val
                165                 170                 175
Asp Ile Ile Ala Pro Arg Ala Ser Gly Thr Ser Met Gly Thr Pro Ile
            180                 185                 190
Asn Asp Tyr Xaa Asn Lys Gly Ser Gly Ser Ser Met Asp Thr Pro His
        195                 200                 205
Val Ser Gly Val Gly Gly Leu Ile Leu Gln Ala His Pro Ser Trp Thr
    210                 215                 220
Pro Asp Lys Val Lys Thr Pro Ser Ser Arg Pro Pro Thr
225                 230                 235
```